(12) United States Patent
Chen et al.

(10) Patent No.: US 10,696,736 B2
(45) Date of Patent: Jun. 30, 2020

(54) BROAD-SPECTRUM MONOCLONAL ANTI-FLU B ANTIBODY AND USES THEREOF

(71) Applicant: XIAMEN UNIVERSITY, Xiamen (CN)

(72) Inventors: Yixin Chen, Xiamen (CN); Chenguang Shen, Xiamen (CN); Junyu Chen, Xiamen (CN); Guosong Wang, Xiamen (CN); Mengya Zhang, Xiamen (CN); Ningshao Xia, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 15/732,536

(22) PCT Filed: Jun. 2, 2016

(86) PCT No.: PCT/CN2016/084496
§ 371 (c)(1),
(2) Date: Nov. 22, 2017

(87) PCT Pub. No.: WO2016/192652
PCT Pub. Date: Dec. 8, 2016

(65) Prior Publication Data
US 2019/0345230 A1 Nov. 14, 2019

(30) Foreign Application Priority Data
Jun. 3, 2015 (CN) .......................... 2015 0 295723

(51) Int. Cl.
| | |
|---|---|
| *A61P 31/16* | (2006.01) |
| *A61K 39/42* | (2006.01) |
| *C12N 5/12* | (2006.01) |
| *C12N 15/11* | (2006.01) |
| *C07K 16/10* | (2006.01) |
| *C07K 16/42* | (2006.01) |
| *C12N 15/63* | (2006.01) |
| *G01N 33/569* | (2006.01) |
| *G01N 33/577* | (2006.01) |
| *A61K 39/00* | (2006.01) |

(52) U.S. Cl.
CPC .......... *C07K 16/1018* (2013.01); *A61K 39/42* (2013.01); *A61P 31/16* (2018.01); *C07K 16/4208* (2013.01); *C12N 5/12* (2013.01); *C12N 15/11* (2013.01); *C12N 15/63* (2013.01); *G01N 33/56983* (2013.01); *G01N 33/577* (2013.01); *A61K 2039/505* (2013.01); *A61K 2039/54* (2013.01); *G01N 2333/11* (2013.01)

(58) Field of Classification Search
None
See application file for complete search history.

(56) References Cited

U.S. PATENT DOCUMENTS

| | | |
|---|---|---|
| 8,834,881 B2 | 9/2014 | Vogels et al. |
| 8,852,595 B2 | 10/2014 | Vogels et al. |
| 8,877,200 B2 | 11/2014 | Shriver et al. |
| 9,005,621 B2 | 4/2015 | Vogels et al. |
| 9,096,657 B2 | 8/2015 | Shriver et al. |
| 9,181,328 B2 | 11/2015 | Yasugi et al. |
| 9,200,064 B2 | 12/2015 | Vogels et al. |
| 2013/0243792 A1 | 9/2013 | Vogels et al. |
| 2013/0302349 A1 | 11/2013 | Shriver et al. |
| 2014/0065165 A1 | 3/2014 | Vogels et al. |
| 2014/0148581 A1 | 5/2014 | Shriver et al. |
| 2014/0341929 A1 | 11/2014 | Vogels et al. |
| 2014/0377262 A1 | 12/2014 | Yasugi et al. |
| 2015/0037345 A1 | 2/2015 | Vogels et al. |
| 2015/0037352 A1 | 2/2015 | Shriver et al. |
| 2016/0002318 A1 | 1/2016 | Vogels et al. |

FOREIGN PATENT DOCUMENTS

| | | |
|---|---|---|
| CN | 104169298 A | 11/2014 |
| CN | 104245731 A | 12/2014 |
| JP | 2015-512867 A | 4/2015 |
| WO | WO 2013/114885 A1 | 8/2013 |
| WO | WO 2013/132007 A1 | 9/2013 |
| WO | WO 2013/170139 A1 | 11/2013 |

OTHER PUBLICATIONS

Huang et al., A Humoral Immunity Survey Following the 2012 Influenza Season After the pH1N1 Pandemic in Guangzhou, China, 2014, Viral Immunology, vol. 27, No. 3, pp. 124-128.*
International Search Report dated Sep. 9, 2016 in PCT/CN2016/084496 filed Jun. 2, 2016.
Extended European Search Report dated Dec. 7, 2018 in European Patent Application No. 16802575.7, citing document AO therein. 11 pages.
Japanese Office Action dated May 22, 2018 in Japanete Patent Applicaton No. 2017-562638, citing documents AO, AP, AX and AY therein, 6 pages.
Dreyfus,C., et al., "Highly Conserved Protective Epitopes on Influenza B Viruses", Science, vol. 337, Sep. 14, 2012, pp. 1343-1348 with cover pages.
Yasugi, M., et al., "Human Monoclonal Antibodies Broadly Neutralizing against Influenza B Virus", PLOS Pathogens, vol. 9, No. 9, Feb. 2013, e1003150, pp. 1-12 with cover page.

* cited by examiner

*Primary Examiner* — Benjamin P Blumel
(74) *Attorney, Agent, or Firm* — Oblon, McClelland, Maier & Neustadt, L.L.P.

(57) ABSTRACT

Provided are a broad-spectrum monoclonal anti-Flu B antibody, cell strains generating the antibody, and a composition comprising the antibody; also provided are uses of the antibody for diagnosing, preventing and/or treating an infection of the Flu B and/or diseases caused by the infection.

17 Claims, 8 Drawing Sheets
(1 of 8 Drawing Sheet(s) Filed in Color)
Specification includes a Sequence Listing.

BROAD-SPECTRUM MONOCLONAL ANTI-FLU B ANTIBODY AND USES THEREOF

The patent or application file contains at least one drawing executed in color. Copies of this patent or patent application publication with color drawing(s) will be provided by the Office upon request and payment of the necessary fee.

TECHNICAL FIELD

The invention relates to the field of immunology and molecular virology, particularly the field of diagnosis, prevention and treatment of Influenza B virus. In particular, the invention relates to a broad-spectrum monoclonal antibody against Influenza B Virus (called Flu B for short), cell strains generating the antibody, and a composition (e.g., a diagnostic agent and a therapeutic agent) comprising the antibody. In addition, the invention also relates to uses of the antibody. The antibody according to the invention is useful for diagnosing, preventing and/or treating Flu B infection and/or a disease (e.g., influenza) caused by the infection.

BACKGROUND ART

Influenza, called "flu" for short, is a respiratory infectious disease caused by influenza virus, and is characterized in clinic by high fever, feeling tired, and muscle pains, accompanied by some respiratory symptoms. Influenza virus is a threat to human health, and the sustained and rapid antigenic drift cause wide spread of seasonal influenza. Common seasonal influenza viruses in human include seasonal H1N1, seasonal H3N2 and influenza B virus. According to WHO statistics, seasonal influenza is responsible for the death of at least 250,000-500,000 persons per year (Peter D. C. et al., J Clin Invest. 2008, 118:3273-3275). In addition, flu outbreak is still an important threat to human beings. Since influenza virus was discovered, flu outbreak occurred five times around the world in human history, resulting in tens of millions of deaths; among them, Spanish influenza pandemics in 1918 resulted in about 20-50 millions of deaths in the world. The influenza pandemics occurred in the 20th century also include Asian influenza (H2N2) outbreak in 1957 and Hong Kong Influenza (H3N2) outbreak in 1968, both of which caused serious public health threat and human social panic (Xu R. et al., Science. 2010, 328: 357-360). In the 21st century, influenza outbreaks still do not stop. Influenza A (2009 pandemic H1N1) outbreak occurred in Mexico in 2009 and quickly spread around the world, which sounded the alarm to human society once again. According to WHO statistics, up to Aug. 6, 2010, a total of 18,449 cases of confirmed deaths were reported in more than 200 countries and regions globally (WHO Pandemic (H1N1) 2009—update 112. 6 Aug. 2010). When the influenza virus outbreak is over, the influenza virus will often evolve into seasonal flu and continue to prevail, and retain harmful to human health by antigenic drift in the epidemic process. In addition, human beings are also threatened by highly pathogenic avian influenza, and highly pathogenic H5N1 avian influenza virus has become one of the greatest infectious diseases that threatens human beings, after "SARS" in 2003. Since 2003, 600 cases of human infected by avian influenza virus H5N1 have been reported globally, among which 353 cases died, with a mortality rate close to 60% (WHO: http://www.who.int/influenza/human_animal_interface/H5N1_cumulative_table_archives/en/index.html). Due to such a high mortality rate, people cannot help worrying that once the virus spreads in human, it will bring a fatal blow to human society. In a word, influenza caused by influenza virus is a serious infectious disease for human.

Influenza virus is an enveloped, single stranded, negative-sense RNA virus that belongs to the genus influenza virus of the family Orthomyxoviridae. Its genome contains eight segments of RNA, and encodes more than 10 viral proteins. According to the difference in antigenicity and genetic characteristics of nucleoprotein (NP) and matrix protein (M), influenza virus can be classified into Influenza A virus, Influenza B virus, and Influenza C virus (Horimoto T. et al., Nat Rev Microbiol, 2005, 3(8): 591-600). Among them, Influenza A Virus (called Flu A for short) has a broad host range, mutates fast, and can cause worldwide pandemics; Influenza B Virus (called Flu B for short) can only infect human and seals, mutates more slowly relative to Influenza A Virus, and can only cause small pandemics in local areas; Influenza C Virus (called Flu C for short) mutates the most slowly, has a weak pathogenicity, and can infect only pregnant women and children having a low resistance generally.

Influenza B virus was first isolated in 1940. Since the 1980s, for influenza B virus, the epidemic is dominated by two lineages that are quite different from each other in terms of antigenicity and genotype, i.e., Victoria lineage and Yamagata lineage. In the 1980s, the epidemic was dominated by the Victoria lineage, and in the 1990s, the epidemic was dominated by the Yamagata lineage. After the year 2000, the epidemics were dominated by both of the two lineages (Jumat M R et al., BMC Res Notes, 2014, 7: 863).

Although the flu epidemic is mainly caused by influenza A virus, influenza B virus is also an important cause for the outbreak of influenza. Among every three influenza epidemic seasons, one is dominated by influenza B virus; and influenza B virus causes diseases and death in a large number of infected patients every year (Lin et al., Virus Res, 2004, 103 (1-2): 47-52). The mortality and morbidity caused by influenza B virus were lower than those of influenza A virus H3N2 subtype, but are higher than those of H1N1 subtype (Dreyfus C. et al., Science, 2012, 337 (6100): 1343-8). Studies have shown that: the clinical symptoms caused by influenza B virus are generally not different from those of influenza A virus (Jumat M R et al., BMC Res Notes, 2014, 7: 863), and the percentage of severe cases caused by influenza B virus was not quite different from that of influenza A virus, either (Su S. et al., Clin Infect Dis, 2014, 59 (2): 252-5). In brief, in recent years, more and more studies have shown that researches on prevention and treatment of influenza B virus are of important significance in clinic.

The first line of defense to prevent influenza is neutralizing antibodies. The vaccine-induced neutralizing antibodies mainly target the protein hemagglutinin (HA) on the surface of virus. HA protein on the surface of virus has a trimeric structure, and each HA monomer consists of HA1 domain and HA2 domain. HA1 forms a globule at the top of the trimer, contains receptor binding sites, and is a region essential for the virus to infect a host cell. HA1 also contains important antigenic sites, can induce generation of protective neutralizing antibodies in organisms, and thus is a key target for vaccine design (Wang T. T. et al., Nat Struct Mol Biol. 2009, 16: 233-234). HA2 is located at the base of the trimer, has a shape of stem, contains fusion peptide, and can mediate the membrane fusion of viral envelope to a host cell. Some monoclonal antibodies against HA2 can inhibit the membrane fusion of influenza virus and achieve the virus-neutralizing effect (Wang T. T. et al., Nat Struct Mol Biol. 2009, 16: 233-234).

Influenza viruses have a high variability, particularly, HA mutates fastest. In current, traditional influenza vaccines are mainly directed to HA protein, and the influenza vaccines become ineffective easily because of virus antigenic drift caused by HA gene mutation. In order to keep influenza vaccines effective, every year WHO needs to monitor the mutation of the prevalent influenza virus strains last year, and decide to continue to use the old influenza virus vaccine strains or establish new influenza virus vaccine strains as candidate strains for influenza vaccines next year, so as to retain the effective resistance to prevalent influenza virus strains by inoculation of new vaccines every year. Therefore, development of "universal vaccines" that are not affected by virus mutation becomes a research focus for development of new vaccines. The glycoprotein on the surface of influenza virus, i.e. "hemagglutinin (HA)", is a main target for the development of universal influenza vaccines and immunotherapeutic medicines against influenza virus. The so-called "universal vaccines" should comprise "highly conserved neutralizing epitopes" shared by different virus variant strains, and can directly induce generation of "broad-spectrum neutralizing antibodies" to combat the infection by different virus variant strains. Therefore, an important route for studying universal influenza vaccines and immunotherapeutic medicines is to look for highly conserved neutralizing epitopes on HA.

In addition, it has been demonstrated that in a mouse model, a humanized anti-HA monoclonal antibody specific for influenza B virus was able to effectively treat experimental mice infected by influenza virus (Yasugi M. et al., PLoS Pathog, 2013, 9(2)). In clinic, polyclonal antibodies and monoclonal antibodies are effective in the prevention of infections by viruses such as Hepatitis A Virus, Hepatitis B Virus, rabies virus and respiratory syncytial virus (Sawyer L. A. et al., Antiviral Res. 2000, 47: 57-77). During Spanish influenza in 1918, it was reported that serum from human in convalescent stage was used in the treatment (Luke T. C. et al., Ann Intern Med. 2006, 145:599-609). The information suggests that antibodies can be used as alternative methods and tools for anti-viral therapy.

Broad-spectrum monoclonal antibodies and highly conserved epitopes against HA of influenza A virus have been reported in many papers. As early as 2009, Throsby et al. reported for the first time that a broad-spectrum neutralizing humanized monoclonal antibody CR6261 recognizing HA2 could neutralize all the influenza viruses belonging to Group 1 (including H1, H2, H5, H6, H8 and H9 subtypes) (Throsby M. et al., PLoS One. 2009, 3: e3942). In 2011, Corti D. et al. also obtained a humanized broad-spectrum neutralizing monoclonal antibody against HA2 by using similar technology, which could neutralize 16 H subtypes of influenza viruses (Corti D. et al., Science. 2011, 333: 850-856). Yoshida et al. reported in 2008 that a broad-spectrum neutralizing monoclonal antibody S139/1 against HA1 could neutralize some influenza virus strains of H1, H2, H3 and H13 subtypes (Yoshida R. et al., PLoS Pathog. 2009, 5: e1000350).

As compared to influenza A virus, broad-spectrum monoclonal antibodies and highly conserved epitopes associated with influenza B virus were rarely reported in the literatures. Until 2012, Dreyfus C et al., found three monoclonal antibodies against HA that could neutralize two lineages of influenza B viruses, i.e., CR8033, CR8071 and CR9114 (Dreyfus C. et al., Science, 2012, 337 (6100): 1343-8). In 2013, Yasugi M et al. found another broad-spectrum neutralizing monoclonal antibody 5A7 against different lineages of Influenza B viruses (Yasugi M. et al., PLoS Pathog, 2013, 9 (2)).

Most of the epitopes recognized by the monoclonal antibodies obtained in the above researches were located in a conserved region near the fusion peptide on HA2 (the primary function of which was to mediate the membrane fusion of influenza virus), instead of HA1 domain having immunodominance in recognition. It increases the uncertainty in the application of these antibodies and the conserved epitopes recognized thereby in the prevention and treatment. Some studies show that the neutralizing monoclonal antibodies recognizing HA2 have the activity of neutralizing natural viruses reduced by 100-1000 folds relative to the activity of neutralizing the pseudotype viruses, the reason may be that it is not easy to have the HA2 epitope of natural virus exposed, and therefore the epitope is not easily accessible (Sui J. et al., Nat Struct Mol Biol. 2009, 16: 265-273; Corti D. et al., J Clin Invest. 2010, 120: 1663-1673).

As compared to HA2, HA1 of influenza virus forms a globule at the top of the trimer, contains a lot of neutralizing epitopes, and is easily accessible. Therefore, looking for broad-spectrum neutralizing epitopes on HA1 is beneficial for development of highly effective broad-spectrum influenza vaccines and therapeutic antibodies. Cyrille Dreyfus et al. reported in 2012 the only one broad-spectrum monoclonal antibody CR8033 so far that recognizes HA1 domain of influenza B virus, however, the monoclonal antibody had hemagglutination-inhibiting activity only against the Yamagata lineage of influenza B virus (Dreyfus C. et al., Science, 2012, 337 (6100): 1343-8.). Therefore, it is of importance and instructive significance for development of broad-spectrum therapeutic antibodies and universal vaccines against influenza B virus, to develop broad-spectrum neutralizing monoclonal antibodies that recognize more highly conserved neutralizing epitopes on HA1 of influenza B virus, and to accurately localize the epitopes. There is need in the art to develop more broad-spectrum monoclonal antibodies that recognize more highly conserved epitopes of HA1 of influenza B virus.

CONTENTS OF INVENTION

In the application, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "antibody" generally refers to an immunoglobulin molecule consisting of two pairs of polypeptide chains (each has a light (L) chain and a heavy (H) chain). Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). A light chain constant region consists of a domain $C_L$. The constant region of an antibody can mediate the binding of an immunoglobulin to a host tissue or factor, including various cells (e.g., effector cells) of an immune system and the first component (C1q) of classical complement system. $V_H$ and $V_L$ region can also be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable regions ($V_H$ and $V_L$) of each heavy/light chain pair form an antigen binding site, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. The term "antibody" is not restricted by any specific method for producing antibodies. For example, antibodies include recombinant antibodies, monoclonal antibodies and polyclonal antibodies. Antibodies may be of different antibody isotypes, for example, IgG (e.g., IgG1, IgG2, IgG3 or IgG4 subtype), IgA1, IgA2, IgD, IgE or IgM antibody.

As used herein, the term "antigen binding fragment" of an antibody refers to a polypeptide comprising a fragment of a full-length antibody, which retain the ability of specifically binding to an antigen that the full-length antibody specifically binds to, and/or compete with the full-length antibody for binding to the same antigen, also known as "antigen binding portion". Generally, see Fundamental Immunology, Ch. 7 (Paul, W., ed., the second edition, Raven Press, N.Y. (1989), which is incorporated herein by reference for all purposes. An antigen binding fragment of an antibody may be produced by recombinant DNA techniques or by enzymatic or chemical cleavage of an intact antibody. Under some conditions, an antigen binding fragment includes Fab, Fab', F(ab')$_2$, Fd, Fv, dAb and complementary determining region (CDR) fragment, single chain antibody (e.g. scFv), chimeric antibody, diabody and such a polypeptide that comprises at least a part of an antibody sufficient to confer the ability of specific binding with the antigen to the polypeptide.

As used herein, the term "Fd fragment" refers to an antibody fragment consisting of $V_H$ and $C_H1$ domain; the term "Fv fragment" refers to an antibody fragment consisting of $V_L$ and $V_H$ domain of a single arm; the term "dAb fragment" refers to an antibody fragment consisting of $V_H$ domain (Ward et al., Nature 341:544-546 (1989)); the term "Fab fragment" refers to an antibody fragment consisting of $V_L$, $V_H$, $C_L$ and $C_H1$ domain; the term "F(ab')$_2$ fragment" refers to an antibody fragment comprising two Fab fragments linked to each other via disulphide bridge(s) on the hinge region.

Under some conditions, an antigen binding fragment of an antibody is a single chain antibody (e.g. scFv), wherein $V_L$ and $V_H$ domains are paired to form a monovalent molecule via a linker that enables them to produce a single polypeptide chain (see, for example, Bird et al., Science 242:423-426 (1988) and Huston et al., Proc. Natl. Acad. Sci. USA 85:5879-5883 (1988)). Such a scFv molecule generally has a common structure: NH$_2$—$V_L$-linker-$V_H$—COOH or NH$_2$—$V_H$-linker-$V_L$—COOH. Suitable linkers in the prior art consist of repeated GGGGS amino acid sequence or variants thereof. For example, a linker having an amino acid sequence (GGGGS)$_4$ may be used, and its variants may also be used (Holliger et al., (1993), Proc. Natl. Acad. Sci. USA 90: 6444-6448). Other linkers that may be used in the invention are described by Alfthan et al., (1995), Protein Eng. 8:725-731, Choi et al., (2001), Eur. J. Immunol. 31: 94-106, Hu et al., (1996), Cancer Res. 56:3055-3061, Kipriyanov et al., (1999), J. Mol. Biol. 293:41-56 and Roovers et al., (2001), Cancer Immunol.

Under some conditions, an antigen binding fragment of an antibody may be a diabody, i.e. a divalent antibody, wherein $V_H$ and $V_L$ domains are expressed on a single polypeptide chain, however, the linker used is too short to allow the pairing of the two domains on the same chain, the domains have to be paired with the complementary domains on another chain to produce two antigen binding sites (see, for example, Holliger P. et al., Proc. Natl. Acad. Sci. USA 90:6444-6448 (1993), and Poljak R. J. et al., Structure 2:1121-1123 (1994)).

An antigen binding fragment (e.g. the antibody fragment as described above) of an antibody may be obtained from a given antibody (e.g., the monoclonal antibodies 12G6, 7G6 and 11B10 provided in the invention) by conventional techniques known by a person skilled in the art (e.g., recombinant DNA technique or enzymatic or chemical cleavage methods), and may be screened for specificity in the same manner by which intact antibodies are screened.

In the invention, unless specified definitely, when the term "antibody" is mentioned, it includes not only an intact antibody, but also an antigen binding fragment of the antibody.

As used herein, the term "mAb" and "monoclonal antibody" refer to an antibody or a fragment of an antibody from a group of highly homologous antibody molecules, i.e. a group of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. Monoclonal antibodies are generally obtained by hybridoma technique reported by Kohler et al. for the first time (Nature, 256:495, 1975), but can also be obtained by recombinant DNA technique (see, for example, U.S. Pat. No. 4,816,567).

For example, monoclonal antibodies may be prepared as follows. Firstly, mice or other suitable host animals are immunized by injection of immunogen (if necessary, adjuvants are added). The injection means of immunogens or adjuvants generally are subcutaneous multi-point injection or intraperitoneal injection. Pre-conjugation of immunogens to some known proteins (e.g. serum albumin or soybean trypsin inhibitor) may promote immunogenicity of antigens in a host. Adjuvants may be Freund's adjuvant or MPL-TDM, etc. After immunization of animal, lymphocytes secreting antibodies that specifically bind to immunogen are produced in the animal. In addition, lymphocytes may be obtained by means of in vitro immunization. Lymphocytes of interest are collected and are fused to myeloma cells using a suitable fusion agent (such as PEG), thereby getting hybridoma cells (Goding, Monoclonal Antibodies: Principles and Practice, pp. 59-103, Academic Press, 1996). The hybridoma cells prepared above are seeded to a suitable culture medium and grow in the medium, and the culture medium comprises one or more substances capable of inhibiting growth of unfused, parent myeloma cells. For example, in the case of parent myeloma cells deficient in hypoxanthine guanine phosphoribosyl transferase (HGPRT or HPRT), growth of HGPRT-deficient cells is inhibited by the addition of substances such as hypoxanthine, aminopterin and thymine (HAT culture medium) to the culture medium. Preferred myeloma cells should have a high fusion rate, stable ability of secreting antibodies, be sensitive to HAT culture medium, and the like. The first choice of myeloma cells is murine myeloma, such as MOP-21 and MC-11 mouse tumor derived cell line (THE Salk Institute Cell Distribution Center, San Diego, Calif. USA), and SP-2/0 or X63-Ag8-653 cell line (American Type Culture Collection, Rockville, Md. USA). In addition, it is also reported that human myeloma and human-mouse heterogeneous myeloma cell lines may be used to prepare human monoclonal antibodies (Kozbor, J. Immunol., 133: 3001 (1984); Brodeur et al., Monoclonal Antibody Production Techniques and Applications, pp. 51-63, Marcel Dekker, Inc., New York, 1987). Culture media for growing hybridoma cells are used to detect the generation of monoclonal antibodies against specific antigens. The following methods may be used to determine the binding specificity of monoclonal antibodies produced in hybridoma cells, immunoprecipitation or in vitro binding assays, such as Radioimmunoassay (RIA) and enzyme linked immunosorbent assay (ELISA). For example, Scatchard assay described in Munson et al., Anal. Biochem. 107: 220 (1980) may be used to determine the affinity of monoclonal antibodies. After determining the specificity, affinity and reactivity of antibodies produced in hybridomas, cell lines of interest may be subcloned by limiting dilution method described in Goding, Monoclonal Antibodies: Principles and Practice, pp. 59-103, Academic Press, 1996. A suitable culture medium may be DMEM or RPMI-1640, etc. In addition, hybridoma cells may grow in a form of ascites tumor in animal bodies. By using traditional methods for purifying immunoglobulins, such as Protein A agarose gel, hydroxyapatite chromatography, gel electrophoresis, dialysis and affinity chromatography, monoclonal antibodies secreted by subclone cells may be isolated from cell culture, ascites or serum.

Monoclonal antibodies may also be obtained by genetic engineering recombinant techniques. The nucleic acid primers that specifically bind to MAb heavy chain and light chain gene are used in PCR amplification, and the DNA molecules encoding MAb heavy chain and light chain can be isolated from hybridoma cells. The DNA molecules obtained are inserted into an expression vector, and host cells (e.g. *E. coli* cells, COS cells, CHO cells, or other myeloma cells that do not produce immunoglobulin) are transfected with them and are cultured under suitable conditions to obtain antibodies of interest by recombinant expression.

As used herein, the term "chimeric antibody" refers to such an antibody wherein a part of its light chain and/or heavy chain is derived from an antibody (which may be originated from a specific species or belongs to a specific antibody type or subtype), and the other part of its light chain and/or heavy chain is derived from another antibody (which may be originated from an identical or different species or belongs to an identical or different antibody type or subtype), provided that the antibody still retains the activity of binding to the antigen of interest (U.S. Pat. No. 4,816,567 to Cabilly et al.; Morrison et al., Proc. Natl. Acad. Sci. USA, 81: 6851-6855 (1984)).

As used herein, the term "humanized antibody" refers to an antibody or antibody fragment in which all the CDR regions or a part of CDR regions of human immunoglobulin (receptor antibody) are replaced with the CDR regions of a non-human antibody (donor antibody), wherein the donor antibody may be non-human (e.g., mouse, rat or rabbit) antibody having the expected specificity, affinity or reactivity. In addition, some amino acids of framework regions (FRs) of a receptor antibody may also be replaced by the corresponding amino acid residues of a non-human antibody, or amino acid residues of another antibody, so as to further improve or optimize the properties of the antibody. With respect to more detailed contents relating to humanized antibodies, see, for example, Jones et al., Nature, 321:522-525 (1986); Reichmann et al., Nature, 332:323-329 (1988); Presta, Curr. Op. Struct. Biol., 2:593-596 (1992); and Clark, Immunol. Today 21: 397-402 (2000).

As used herein, the term "neutralization antibody" refers to an antibody or antibody fragment that can eliminate or significantly reduce virulence (e.g. ability of infecting a cell) of a virus of interest.

As used herein, the term "epitope" refers to a part on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric configuration, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein.

As used herein, the term "epitope peptide" refers to peptide fragment on antigen that acts as epitope. Under some conditions, epitope peptide alone can be specifically recognized/bound by an antibody against the epitope. Under some other conditions, epitope peptide has to be fused to a carrier protein so that the epitope can be specifically recognized by an antibody. As used herein, the term "carrier protein" refers to such a protein that may act as a carrier of epitope peptide, i.e. the epitope peptide may be inserted into the protein at a specific position (for example, inner, N-terminal or C-terminal of the protein), so that the epitope peptide can be presented and thus can be recognized by an antibody or immune system. Such carrier proteins are well known by a person skilled in the art, including, for example, HPV L1 protein (into which the epitope peptide may be inserted between amino acids from positions 130 to 131 or amino acids from positions 426 to 427 of the protein, see Slupetzky, K. et al., Chimeric papillomavirus-like particles expressing a foreign epitope on capsid surface loops [J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16 [J]. J Virol, 2003, 77: 8386-8393), HBV core antigen (the amino acids from positions 79 to 81 of the protein may be replaced with the epitope peptide, see, Koletzki, D., et al. HBV core particles allow the insertion and surface exposure of the entire potentially protective region of Puumala hantavirus nucleocapsid protein [J]. Biol Chem, 1999, 380: 325-333), woodchuck hepatitis virus core protein (the amino acids from positions 79 to 81 of the protein may be replaced with the epitope peptide, see, Sabine Konig, Gertrud Beterams and Michael Nassal, *J. Virol.* 1998, 72(6):4997), and CRM197 protein (the epitope peptide may be linked to the N-terminal or C-terminal of the protein or a fragment thereof). Optionally, a linker (e.g., a flexible or rigid linker) may be used between an epitope peptide and a carrier protein to promote their respective folding.

Antibodies may be screened depending on competitiveness of binding to the same epitope by conventional techniques known by a person skilled in the art. For example, researches on competition or cross-competition may be conducted to obtain antibodies that compete or cross-compete with each other for binding to an antigen (e.g. influenza virus HA protein). High-throughput methods for obtaining antibodies binding to the same epitope, which are based on their cross-competition, are described in an international patent application WO 03/48731. Therefore, antibodies and antigen binding fragments (i.e. antigen binding parts) thereof, which compete with monoclonal antibodies according to the invention (e.g. monoclonal antibody 12G6, 7G6 or 11B10) for binding to the same epitopes on influenza virus HA protein, can be obtained by conventional techniques known by a person skilled in the art.

As used herein, the term "isolated" refers to a state obtained from natural state by artificial means. If a certain "isolated" substance or component is present in nature, it is possible because its natural environment changes, or the substance is isolated from the natural environment, or both. For example, a certain non-isolated polynucleotide or polypeptide naturally exists in a certain living animal body, and the same polynucleotide or polypeptide with a high purity isolated from such a natural state is called an isolated polynucleotide or polypeptide. The term "isolated" excludes neither the mixed artificial or synthesized substance nor other impure substances that do not affect the activity of the isolated substance.

As used herein, the term "E. coli expression system" refers to an expression system consisting of E. coli (strain) and a vector, wherein the E. coli (strain) are derived from the commercially available strains, including, but not limited to: GI698, ER2566, BL21 (DE3), B834 (DE3), and BLR (DE3).

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, prokaryotic cell such as E. coli or Bacillus subtilis, fungal cell such as yeast cell or Aspergillus, insect cell such as S2 Drosophila cell or Sf9, and animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng.

12(10): 879-884 (1999); and Burks et al., Proc. Natl. Acad. Sci. USA 94: 412-417 (1997), which are incorporated herein by reference).

As used herein, the term "immunogenicity" refers to ability of stimulating formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

As used herein, the term "specifically bind" refers to the binding of two molecules in a non-random manner, such as the reaction between an antibody and the antigen it directs to. In some embodiments, an antibody that specifically binds to an antigen (or an antibody specific for an antigen) refers to an antibody that binds to the antigen with an affinity ($K_D$) of less than about $10^{-5}$ M, e.g. of less than about $10^{-6}$ M, $10^{-7}$ M, $10^{-8}$ M, $10^{-9}$ M or $10^{-10}$ M or less.

As used herein, the term "$K_D$" refers to a dissociation equilibrium constant of a specific antibody-antigen interaction, which is used to describe the binding affinity of an antibody to an antigen. The smaller the dissociation equilibrium constant is, the more closely the antibody binds to the antigen and the higher the affinity of the antibody to the antigen is. Generally, an antibody (e.g., the monoclonal antibody 12G6, 7G6 or 11B10 according to the invention) binds to an antigen (e.g., HA protein of influenza virus) with a $K_D$ of less than about $10^{-5}$ M, e.g., less than about $10^{-6}$ M, $10^{-7}$ M, $10^{-8}$ M, $10^{-9}$ M or $10^{-10}$ M or less, determined by, for example, surface plasmon resonance (SPR) in BIA-CORE device.

As used herein, the term "monoclonal antibody" and the term "MAb" have the same meanings and are used interchangeably; the term "polyclonal antibody" and the term "PAb" have the same meanings and are used interchangeably; the term "polypeptide" and "protein" have the same meanings and are used interchangeably. Moreover, in the invention, amino acids are generally represented by single letter codes or three letter codes. For example, alanine may be represented by A or Ala.

As used herein, the term "hybridoma" and the term "hybridoma cell line" may be used interchangeably. When the term "hybridoma" and the term "hybridoma cell line" are mentioned, they also include subclone and progeny cell of hybridoma. For example, when hybridoma cell line 12G6, 7G6 or 11B10 is mentioned, it also refers to the subclone and progeny cell of hybridoma cell line 12G6, 7G6 or 11B10.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

As used herein, the term "protein vaccine" refers to a polypeptide-based vaccine, optionally comprising an adjuvant. Polypeptides in vaccines may be obtained by genetic engineering techniques or by methods of chemical synthesis. As used herein, the term "nucleic acid vaccine" refers to a DNA or RNA-based vaccine (such as plasmid, e.g., expression plasmid), optionally comprising an adjuvant.

As used herein, the term "an effective amount" refers to an amount that is sufficient to achieve or at least partially achieve the expected effect. For example, an amount effective for preventing a disease (such as influenza virus infection or diseases associated with influenza virus infection) refers to an amount effective for preventing, suppressing, or delaying the occurrence of a disease (such as influenza virus infection or diseases associated with influenza virus infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

As used herein, the terms "Yamagata lineage" and "Yamagata lineage of influenza B virus" refer to an influenza B virus lineage that belongs to the same evolutionary branch as the representative strain of influenza B virus B/Yamagata/16/1988 in terms of antigenicity and evolutionary relationship of HA protein; which includes the following exemplary strains: B/Harbin/7/1994, B/Florida/4/2006, B/Xiamen/891/206, B/Xiamen/756/2007, B/Xiamen/1147/2008, B/Xiamen/N697/2012. The terms "Yamagata lineage" and "Yamagata lineage of influenza B virus" have the same meanings, and can be used interchangeably.

As used herein, the terms "Victoria lineage" and "Victoria lineage of influenza B virus" refer to an influenza B virus lineage that belongs to the same evolutionary branch as the representative strain of influenza B virus B/Victoria/2/1987 in terms of antigenicity and evolutionary relationship of HA protein; which includes, but is not limited to the following exemplary strains: B/Hong Kong/330/2001, B/Malaysia/2506/2004, B/Xiamen/3043/2006, B/Xiamen/165/2007, B/Brisbane/60/2008, B/Brisbane/33/2008, B/Xiamen/1346/2008, B/Xiamen/N639/2010, and B/Xiamen/N678/2012. The terms "Victoria lineage" and "Victoria lineage of influenza B virus" have the same meanings, and can be used interchangeably.

As used herein, the term "hemagglutinin" and "HA protein" refers to an antigenic glycoprotein encoded by Fragment 4 of influenza virus genome, which is present on the surface of viromembrane, is synthesized in endocytoplasmic reticulum, and has a molecular weight of about 76 kD. HA protein can be hydrolyzed into HA1 polypeptide (with a molecular weight of 47 kD, also called "HA1 domain" herein) and HA2 polypeptide (with a molecular weight of 29 kD, also called "HA2 domain" herein), and they are connected via a disulfide bond to form a HA molecule having a typical Type I membrane protein structure. Hemagglutinin has immunogenicity, and anti-hemagglutinin antibodies can be used to neutralize influenza virus. Hemagglutinin is well known by a person skilled in the art, and its amino acid sequence can be found in various public databases, such as NCBI. HA1 polypeptide/domain forms a globule at the top of HA protein, contains the receptor binding sites of a virus, can bind to the sialic acid receptors on the membrane of a host cell, and thereby mediate the entry of the virus into the cell. HA2 polypeptide/domain can assist the membrane fusion of viral envelope to a host cell, and play an important role in the entry of a virus into a host cell.

As used herein, the term "hemagglutination-inhibiting activity" refers to a functional activity of an antibody or an antigen binding fragment thereof to inhibit the blood clotting caused by the binding of HA protein of influenza virus to the sialic acid receptor on the surface of red blood cells. An antibody or an antigen binding fragment thereof having hemagglutination-inhibiting activity can inhibit the binding of a virus to a cell receptor.

As used herein, the term "neutralizing activity" refers to the functional activity of an antibody or an antigen binding fragment thereof binding to an antigen protein on a virus, thereby reducing or inhibiting the virulence (e.g., the ability of infecting a cell) of a target virus. An antibody or an antigen binding fragment thereof having neutralizing activity can prevent the infection of a cell by a virus and/or the maturation of a progeny virus and/or the release of a progeny virus.

The inventor surprisingly found by conducting a lot of experimental researches that there were highly conserved neutralizing epitopes in HA1 domain of the surface antigen HA protein of influenza B virus, and the antibodies recognizing these epitopes could bind to HA protein of different lineages of influenza viruses and specifically bind to HA protein of Yamagata lineage and Victoria lineage of influenza B viruses, and showed a broad-spectrum virus-binding reactivity and a broad-spectrum virus-neutralizing ability. Therefore, the antibodies according to the invention are particularly suitable for diagnosing, preventing and treating an infection by influenza B virus or a disease (e.g., influenza) associated with the infection.

In an aspect, the invention provides a monoclonal antibody or an antigen binding fragment thereof, comprising complementary determining regions (CDR) of a heavy chain variable region (VH) which are selected from:
(1) VH CDR1-3 with amino acid sequences set forth in SEQ ID NO: 1-3, respectively;
(2) VH CDR1-3 with amino acid sequences set forth in SEQ ID NO: 7-9, respectively; and
(3) VH CDR1-3 with amino acid sequences set forth in SEQ ID NO: 13-15, respectively;
and/or,
complementary determining regions (CDR) of a light chain variable region (VL) which are selected from:
(4) VL CDR1-3 with amino acid sequences set forth in SEQ ID NO: 4-6, respectively;
(5) VL CDR1-3 with amino acid sequences set forth in SEQ ID NO: 10-12, respectively; and
(6) VL CDR1-3 with amino acid sequences set forth in SEQ ID NO: 16-18, respectively.

In some preferred embodiments, the monoclonal antibody comprises a heavy chain variable region (VH) selected from:
(1) VH set forth in SEQ ID NO: 19;
(2) VH set forth in SEQ ID NO: 21; and
(3) VH set forth in SEQ ID NO: 23.

In some preferred embodiments, the monoclonal antibody comprises a light chain variable region (VL) selected from:
(1) VL set forth in SEQ ID NO: 20;
(2) VL set forth in SEQ ID NO: 22; and
(3) VL set forth in SEQ ID NO: 24.

In some preferred embodiments, the monoclonal antibody comprises:
(1) VH CDR1-3 with amino acid sequences set forth in SEQ ID NO: 1-3, respectively, and VL CDR1-3 with amino acid sequences set forth in SEQ ID NO: 4-6, respectively;
(2) VH CDR1-3 with amino acid sequences set forth in SEQ ID NO: 7-9, respectively, and VL CDR1-3 with amino acid sequences set forth in SEQ ID NO: 10-12, respectively; or
(3) VH CDR1-3 with amino acid sequences set forth in SEQ ID NO: 13-15, respectively, and VL CDR1-3 with amino acid sequences set forth in SEQ ID NO: 16-18, respectively.

In some preferred embodiments, the monoclonal antibody comprises:
(1) VH set forth in SEQ ID NO: 19 and VL set forth in SEQ ID NO: 20;
(2) VH set forth in SEQ ID NO: 21 and VL set forth in SEQ ID NO: 22; or
(3) VH set forth in SEQ ID NO: 23 and VL set forth in SEQ ID NO: 24.

In some preferred embodiments, the monoclonal antibody or antigen binding fragment thereof is selected from Fab, Fab', F(ab')$_2$, Fd, Fv, dAb, complementary determining region fragment, single chain antibody (e.g., scFv), mouse antibody, rabbit antibody, humanized antibody, full-human antibody, chimeric antibody (e.g., human mouse chimeric antibody), or bispecific or poly-specific antibody.

In some preferred embodiments, the monoclonal antibody comprises a non-CDR region, and the non-CDR region is from a species other than murine, e.g., from human antibody.

In some preferred embodiments, the monoclonal antibody is a monoclonal antibody produced by Hybridoma cell line 12G6, 7G6 or 11B10, the Hybridoma cell line 12G6, 7G6 and 11B10 have been deposited in China Center for Type Culture Collection (CCTCC), and have a deposition number of CCTCC NO:C201527, CCTCC NO:C201435 and CCTCC NO: C201432, respectively.

In some preferred embodiments, the monoclonal antibody or antigen binding fragment thereof can specifically bind to HA1 domain of HA protein of at least two lineages of influenza B viruses. In some preferred embodiments, the monoclonal antibody or antigen binding fragment thereof can specifically bind to HA1 domain of HA protein of Yamagata lineage and Victoria lineage of influenza B viruses. In some preferred embodiments, the monoclonal antibody or antigen binding fragment thereof has hemagglutination-inhibiting activity against Yamagata lineage of influenza B virus and Victoria lineage of influenza B virus. In some preferred embodiments, the monoclonal antibody or antigen binding fragment thereof has neutralizing activity, and can neutralize Yamagata lineage of influenza B virus and Victoria lineage of influenza B virus.

In some preferred embodiments, the monoclonal antibody or antigen binding fragment thereof has one or more of the following activities: (a) inhibiting entry of at least two lineages of influenza B viruses (e.g., Yamagata lineage and Victoria lineage of influenza B viruses) into a host cell; (b) inhibiting release of at least two lineages of influenza B viruses (e.g., Yamagata lineage and Victoria lineage of influenza B viruses) from a host cell; (c) inhibiting membrane fusion of at least two lineages of influenza B viruses (e.g., Yamagata lineage and Victoria lineage of influenza B viruses) to a host cell; (d) triggering ADCC against at least two lineages of influenza B viruses (e.g., Yamagata lineage and Victoria lineage of influenza B viruses); and (e) triggering CDC against at least two lineages of influenza B viruses (e.g., Yamagata lineage and Victoria lineage of influenza B viruses). In some preferred embodiments, the monoclonal antibody or antigen binding fragment thereof has at least 1, at least 2, at least 3, at least 4, or 5 of the above activities. In some preferred embodiments, the monoclonal antibody or antigen binding fragment thereof have all the five activities. In some preferred embodiments, the monoclonal antibody or antigen binding fragment thereof neutralizes influenza B virus by said 5 activities, and thereby prevents and treats Flu B infection.

In another aspect, the invention provides a monoclonal antibody or an antigen binding fragment thereof, which can block/inhibit, by at least 50%, preferably at least 60%, preferably at least 70%, preferably at least 80%, preferably at least 90%, preferably at least 95% or preferably at least 99%, the binding of influenza B virus or HA protein thereof to a monoclonal antibody selected from a group consisting of:

(1) a monoclonal antibody produced by Hybridoma cell line 12G6, the Hybridoma cell line 12G6 has been deposited in China Center for Type Culture Collection (CCTCC), and has a deposition number of CCTCC NO:C201527;

(2) a monoclonal antibody produced by Hybridoma cell line 7G6, the Hybridoma cell line 7G6 has been deposited in China Center for Type Culture Collection (CCTCC), and has a deposition number of CCTCC NO:C201435; and (3) a monoclonal antibody produced by Hybridoma cell line 11B10, the Hybridoma cell line 11B10 has been deposited in China Center for Type Culture Collection (CCTCC), and has a deposition number of CCTCC NO:C201432.

In some preferred embodiments, the monoclonal antibody or antigen binding fragment thereof can specifically bind to HA1 domain of HA protein of at least two lineages of influenza B viruses. In some preferred embodiments, the monoclonal antibody or antigen binding fragment thereof can specifically bind to HA1 domain of HA protein of Yamagata lineage and Victoria lineage of influenza B viruses. In some preferred embodiments, the monoclonal antibody or antigen binding fragment thereof has hemagglutination-inhibiting activity against Yamagata lineage of influenza B virus and Victoria lineage of influenza B virus. In some preferred embodiments, the monoclonal antibody or antigen binding fragment thereof has neutralizing activity, and can neutralize Yamagata lineage of influenza B virus and Victoria lineage of influenza B virus.

In some preferred embodiments, the monoclonal antibody or antigen binding fragment thereof has one or more of the following activities: (a) inhibiting entry of at least two lineages of influenza B viruses (e.g., Yamagata lineage and Victoria lineage of influenza B viruses) into a host cell; (b) inhibiting release of at least two lineages of influenza B viruses (e.g., Yamagata lineage and Victoria lineage of influenza B viruses) from a host cell; (c) inhibiting membrane fusion of at least two lineages of influenza B viruses (e.g., Yamagata lineage and Victoria lineage of influenza B viruses) to a host cell; (d) triggering ADCC against at least two lineages of influenza B viruses (e.g., Yamagata lineage and Victoria lineage of influenza B viruses); and (e) triggering CDC against at least two lineages of influenza B viruses (e.g., Yamagata lineage and Victoria lineage of influenza B viruses). In some preferred embodiments, the monoclonal antibody or antigen binding fragment thereof has at least 1, at least 2, at least 3, at least 4, or 5 of the above activities. In some preferred embodiments, the monoclonal antibody or antigen binding fragment thereof has all the 5 activities. In some preferred embodiments, the monoclonal antibody or antigen binding fragment thereof neutralizes influenza B virus by said 5 activities, and thereby prevents and treats Flu B infection.

The epitope recognized by such a monoclonal antibody is the same as, or sterically overlaps with, that recognized by the monoclonal antibody 12G6, 7G6 or 11B10, so that such a monoclonal antibody can reduce the binding of the monoclonal antibody 12G6, 7G6 or 11B10 to HA1 domain of HA protein by at least 50%, preferably at least 60%, preferably at least 70%, preferably at least 80%, preferably at least 90%, preferably at least 95% or preferably at least 99%.

Conventional methods such as the method as described in Antibodies: A Laboratory Manual, Cold Spring Harbor Laboratory, Ed Harlow and David Lane (1988), may be used to determine the ability of a certain monoclonal antibody to be tested to reduce the binding of a known monoclonal antibody to an antigen (e.g., HA protein of influenza B virus). An exemplary method comprises: pre-coating an antigen onto a microwell plate, adding an unlabeled antibody to be tested, which has been subjected to serial dilution, and a known labelled monoclonal antibody at a specific concentration, to the pre-coated microwell plate to carry out incubation, and then determining the number of the known antibodies bound to the plate after washing, in the presence of the antibody to be tested at a different dilution degree. The stronger the ability of the antibody to be tested to compete with the known antibody for binding to the antigen is, the weaker the ability of the known antibody to bind to the antigen is, and the less the number of the known antibodies bound to the plate is. In general, an antigen is pre-coated onto a 96-well microplate, and radioactive labelling methods or enzyme labelling methods are used to determine the ability of a monoclonal antibody to be tested to block a known labelled monoclonal antibody.

By methods known in the art, the monoclonal antibody according to the invention can be used to produce an anti-idiotype antibody (Schulman J L. et al., Monographs in allergy, 1986, 22:143-9). An anti-idiotype antibody is an antibody that specifically recognize/bind to the idiotype of the antibody for preparing the idiotype antibody (i.e., the idiotype of the variable region of the antibody for preparing the idiotype antibody is used as an antigen epitope), and can simulate/reconstruct the antigen epitope recognized by the antibody for preparing the idiotype antibody. The monoclonal antibody according to the invention can also be used to prepare such an anti-idiotype antibody, and the anti-idiotype antibody thus obtained is also included in the scope of the invention. Therefore, in one aspect, the invention further provides an anti-idiotype antibody, which is specifically directed to the idiotype of the monoclonal antibody according to the invention.

The invention also provides an isolated nucleic acid molecule, encoding the monoclonal antibody or antigen binding fragment thereof according to the invention. The nucleic acid molecule can be isolated from a hybridoma cell, or can be obtained by genetic engineering recombinant technique or method of chemical synthesis.

Therefore, in another aspect, the invention provides an isolated nucleic acid molecule, comprising a nucleic acid sequence capable of encoding a heavy chain variable region of an antibody, wherein the heavy chain variable region comprises:

(1) VH CDR1-3 with amino acid sequences set forth in SEQ ID NO: 1-3, respectively;

(2) VH CDR1-3 with amino acid sequences set forth in SEQ ID NO: 7-9, respectively; or (3) VH CDR1-3 with amino acid sequences set forth in SEQ ID NO: 13-15, respectively.

In some preferred embodiments, the heavy chain variable region has the amino acid sequence set forth in SEQ ID NO: 19, SEQ ID NO: 21 or SEQ ID NO: 23.

In some preferred embodiments, the nucleic acid molecule has the nucleotide sequence set forth in SEQ ID NO: 25, SEQ ID NO: 27 or SEQ ID NO: 29.

In another aspect, the invention provides an isolated nucleic acid molecule, comprising a nucleic acid sequence capable of encoding a light chain variable region of an antibody, wherein the light chain variable region comprises:

(1) VL CDR1-3 with amino acid sequences set forth in SEQ ID NO: 4-6, respectively;

(2) VL CDR1-3 with amino acid sequences set forth in SEQ ID NO: 10-12, respectively; or (3) VL CDR1-3 with amino acid sequences set forth in SEQ ID NO: 16-18, respectively.

In some preferred embodiments, the light chain variable region has the amino acid sequence set forth in SEQ ID NO: 20, SEQ ID NO: 22 or SEQ ID NO: 24.

In some preferred embodiments, the nucleic acid molecule has the nucleotide sequence set forth in SEQ ID NO: 26, SEQ ID NO: 28 or SEQ ID NO: 30.

In another aspect, the invention provides an isolated nucleic acid molecule, comprising a nucleic acid sequence capable of encoding the heavy chain variable region as defined above, and a nucleic acid sequence encoding the light chain variable region as defined above.

In another aspect, the invention provides an isolated nucleic acid molecule encoding the monoclonal antibody or antigen binding fragment thereof according to the invention as defined above.

In another aspect, the invention provides a vector comprising the isolated nucleic acid molecule as defined above. The vector according to the invention may be a cloning vector, or an expression vector.

In some preferred embodiments, the vector according to the invention is, for example, a plasmid, a cosmid, a phage, etc.

In another aspect, the invention also provides a host cell comprising the isolated nucleic acid molecule or vector according to the invention. Such a host cell includes, but is not limited to, a prokaryotic cell such as E. coli cell, and an eukaryotic cell such as yeast cell, an insect cell, a plant cell and an animal cell (such as mammalian cell, e.g., mouse cell, human cell, etc.). The cell according to the invention may be a cell line, such as 293T cell.

In another aspect, the invention provides a method for producing the monoclonal antibody or antigen binding fragment thereof according to the invention, comprising culturing the host cell according to the invention under a suitable condition, and recovering the monoclonal antibody or antigen binding fragment thereof according to the invention from the cell culture.

In another aspect, the invention provides a hybridoma cell line selected from:

1) Hybridoma cell line 12G6, deposited in China Center for Type Culture Collection (CCTCC), with a deposition number of CCTCC NO: C201527;

2) Hybridoma cell line 7G6, deposited in China Center for Type Culture Collection (CCTCC), with a deposition number of CCTCC NO: C201435; and 3) Hybridoma cell line 11B10, deposited in China Center for Type Culture Collection (CCTCC), with a deposition number of CCTCC NO: C201432.

As demonstrated in the present application, the amino acid sequence of the heavy chain variable region of the monoclonal antibody 12G6 is set forth in SEQ ID NO: 19 (its exemplary nucleotide sequence is set forth in SEQ ID NO: 25), and the amino acid sequence of the light chain variable region is set forth in SEQ ID NO: 20 (its exemplary nucleotide sequence is set forth in SEQ ID NO: 26).

The amino acid sequences of the heavy chain CDR1, CDR2 and CDR3 of the monoclonal antibody 12G6 are SEQ ID NO:1-3, respectively; the amino acid sequences of the light chain CDR1, CDR2 and CDR3 are SEQ ID NO:4-6, respectively.

As demonstrated in the present application, the amino acid sequence of the heavy chain variable region of the monoclonal antibody 7G6 is set forth in SEQ ID NO: 21 (its exemplary nucleotide sequence is set forth in SEQ ID NO: 27), and the amino acid sequence of the light chain variable region is set forth in SEQ ID NO: 22 (its exemplary nucleotide sequence is set forth in SEQ ID NO: 28).

The amino acid sequences of the heavy chain CDR1, CDR2 and CDR3 of the monoclonal antibody 7G6 are SEQ ID NO: 7-9, respectively; the amino acid sequences of the light chain CDR1, CDR2 and CDR3 are SEQ ID NO: 10-12, respectively.

As demonstrated in the present application, the amino acid of the heavy chain variable region sequence of the monoclonal antibody 11B10 is set forth in SEQ ID NO: 23 (its exemplary nucleotide sequence is set forth in SEQ ID NO: 29), and the amino acid sequence of the light chain variable region is set forth in SEQ ID NO: 24 (its exemplary nucleotide sequence is set forth in SEQ ID NO: 30).

The amino acid sequences of the heavy chain CDR1, CDR2 and CDR3 of monoclonal antibody 11B10 are SEQ ID NO: 13-15, respectively; the amino acid sequences of the light chain CDR1, CDR2 and CDR3 are SEQ ID NO:16-18, respectively.

In another aspect, the invention provides a composition comprising the monoclonal antibody or antigen binding fragment thereof, the anti-idiotype antibody, the isolated nucleic acid molecule, the vector or the host cell as described above.

In another aspect, the invention provides a kit comprising the monoclonal antibody or antigen binding fragment thereof according to the invention. In some preferred embodiments, the monoclonal antibody or antigen binding fragment thereof according to the invention may also comprise a detectable marker. In some preferred embodiments, the kit further comprises a second antibody that specifically recognizes the monoclonal antibody or antigen binding fragment thereof according to the invention. Preferably, the second antibody further comprises a detectable marker. Such a detectable marker, which is well known by a person skilled in the art, includes, but is not limited to, a radioisotope, a fluorescent substance, a luminescent substance, a chromophoric substance or an enzyme (e.g., horseradish peroxidase), etc.

In another aspect, the invention provides a method for detecting the presence or level of influenza B virus or HA protein thereof in a sample, comprising using the monoclonal antibody or antigen binding fragment thereof according to the invention. In some preferred embodiments, the monoclonal antibody or antigen binding fragment thereof according to the invention further comprises a detectable marker. In another preferred embodiment, the method further comprises using a second antibody carrying a detectable marker to detect the monoclonal antibody or antigen binding fragment thereof according to the invention. The method may be used for diagnostic purpose (for example, said sample is a sample from a patient) or for non-diagnostic purpose (for example, said sample is a cell sample, rather than a sample from a patient). In some preferred embodiments, the influenza B virus is selected from Yamagata lineage and Victoria lineage of influenza B viruses.

In another aspect, the invention provides a method for diagnosing whether a subject is infected by influenza B virus, comprising: using the monoclonal antibody or antigen binding fragment thereof according to the invention to detect the presence of influenza B virus or HA protein thereof in a sample from the subject. In some preferred embodiments, the monoclonal antibody or antigen binding fragment thereof according to the invention further comprises a detectable marker. In another preferred embodiment, the method further comprises using a second antibody carrying a detectable marker to detect the monoclonal antibody or antigen binding fragment thereof according to the invention. Preferably, the influenza B virus is selected from Yamagata lineage and Victoria lineage of influenza B viruses.

In another aspect, the invention provides use of the monoclonal antibody or antigen binding fragment thereof according to the invention in the manufacture of a kit for detecting the presence or level of influenza B virus or HA protein thereof in a sample, or for diagnosing whether a subject is infected by influenza B virus. Preferably, the influenza B virus is selected from Yamagata lineage and Victoria lineage of influenza B viruses.

In some preferred embodiments, the sample includes, but is not limited to the excreta, buccal and nasal secretion from a subject (e.g., a mammal, preferably human).

In some preferred embodiments, the monoclonal antibody is such an antibody, comprising: VH CDR1-3 with amino acid sequences set forth in SEQ ID NO: 1-3, respectively, and/or VL CDR1-3 with amino acid sequences set forth in SEQ ID NO: 4-6, respectively; preferably, comprising: VH set forth in SEQ ID NO: 19 and/or VL set forth in SEQ ID NO: 20; more preferably, is the monoclonal antibody 12G6.

In some preferred embodiments, the monoclonal antibody is such an antibody, comprising: VH CDR1-3 with amino acid sequences set forth in SEQ ID NO: 7-9, respectively, and/or VL CDR1-3 with amino acid sequences set forth in SEQ ID NO: 10-12, respectively; preferably, comprising: VH set forth in SEQ ID NO: 21 and/or VL set forth in SEQ ID NO: 22; more preferably, is the monoclonal antibody 7G6.

In some preferred embodiments, the monoclonal antibody is such an antibody, comprising: VH CDR1-3 with amino acid sequences set forth in SEQ ID NO: 13-15, respectively, and/or VL CDR1-3 with amino acid sequences set forth in SEQ ID NO: 16-18, respectively; preferably, comprising: VH set forth in SEQ ID NO: 23 and/or VL set forth in SEQ ID NO: 24; more preferably, is the monoclonal antibody 11B10.

Common methods for determining the presence or level of a target virus or antigen (e.g., influenza B virus or HA protein thereof) in a sample by using an antibody or an antigen binding fragment thereof are well known by a person skilled in the art. In some preferred embodiments, the methods may utilize enzyme-linked immunosorbent assay (ELISA), enzyme immunoassay, chemiluminescence immunoassay, radioimmunodetection, fluorescent immunoassay, immunochromatography, competition methods and similar detection methods.

In some preferred embodiments, the detection methods may comprise the following steps: (i) under a condition that allows the binding of an antibody or an antigen binding fragment thereof to a target virus or antigen (i.e., influenza B virus or HA protein thereof) to form a complex of an antibody or an antigen binding fragment thereof and influenza B virus or HA protein thereof, contacting the monoclonal antibody or antigen binding fragment thereof according to the invention with a sample to be tested; and (ii) determining the presence of the complex, so as to determine whether the sample comprises influenza B virus or HA protein thereof.

In some preferred embodiments, the detection methods may comprise the following steps: (i) absorbing a first antibody onto a solid support; (ii) adding a test sample suspected of containing influenza B virus or HA protein thereof, to the support; (iii) adding a second antibody carrying a marker, to the support; and (iv) detecting the presence of the marker so as to determine whether influenza B virus or HA protein thereof is present in the sample.

In addition, based on the principle of competition methods or sandwich methods, said detection methods may be used to detect a target antigen or antibody.

Competition methods are used to compare the quantitative relation between an antigen in a sample and a known amount of a labeled antigen that competes with the former for binding to the monoclonal antibody according to the invention. Competition method-based immunoassay generally comprises adding a sample containing a target antigen in an unknown amount, and a labeled target antigen in a predetermined amount, to a solid support onto which the monoclonal antibody according to the invention has been coated by known physical or chemical methods; and then, after incubation for a period of time, washing the support, and determining the amount or level of the marker bound onto the support.

In sandwich methods, the target antigen in a sample is sandwiched between a coated monoclonal antibody and a labeled monoclonal antibody, and then by determining the amount or level of the marker of the labeled monoclonal antibody, the presence of the antigen can be determined quantitatively. For example, sandwich method-based immunoassay may comprise, adding a sample containing a target antigen in an unknown amount to a solid support onto which the monoclonal antibody according to the invention has been coated by physical or chemical methods, to carry out a reaction; then, adding the labeled monoclonal antibody according to the invention to carry out a reaction; and after incubation for a period of time, washing the support, and determining the amount or level of the marker bound onto the support.

The marker may be a radioisotope, an enzyme, an enzyme substrate, a luminescent substance such as isoluminol and acridinium ester, a fluorescent substance such as fluorescein and rhodamine, a chromophoric substance such as latex particle and colloidal gold. For example, an enzyme for use in labeling includes, but is not limited to, peroxidase (such as horseradish peroxidase HRP), alkaline phosphatase, β galactosidase, acetylcholinesterase and glucose oxidase. Suitable enzyme substrates include, but are not limited to, for example, 2,2'-azino-bis(3-ethylbenzothiazoline-6-sulfonate), luminol-hydrogen peroxide, o-phenylenediamine-hydrogen peroxide (directed to peroxidase), para-nitro-phenyl phosphate, 4-methylumbelliferyl phosphate, 3-(2'-spiroadamantane)-4-methoxy-4-(3"-phosphoryloxy)phenyl-1,2-dioxetane (directed to alkaline phosphatase), p-nitrophenyl-β-D-galactopyranoside and 4-methylumbelliferyl-β-D-galactose (directed to beta galactosidase). Fluorescent substance for use in labeling includes, but is not limited to, fluorescein, fluorescein isothiocyanate, rhodamine, tetramethyl rhodamine, eosin, green fluorescent protein, phycoerythrin, coumarin, methylcoumarin, pyrene, malachite green, toluylene, lucifer yellow, Cascade blue, [5-(4,6-dichlorotriazinyl)aminofluorescein], dansyl chloride, phycoerythrin, fluorescent lanthanide complexes, Cy3, Cy5, etc. Radioisotope includes, but is not limited to, $^{14}C$, $^{123}I$, $^{124}I$, $^{131}I$, $^{35}S$ or $^3H$.

Other markers include, but are not limited to, quantum dot label, chromophore label, affinity ligand label, electromagnetic spin label, heavy atom label, epitope tag (such as FLAG or HA epitope), and a binding pair capable of forming a complex (e.g., streptavidin/biotin, avidin/biotin or antigen/antibody complex (e.g., rabbit IgG and anti-rabbit IgG)).

Methods for binding a marker to an antigen or antibody are known in the art, including, but not limited to, maleimide method (J. Biochem. (1976), 79, 233), biotin activation method (J. Am. Chem. Soc. (1978), 100, 3585), hydrophobic binding method, ester activation method or isocyanate method ("Enzyme immunoassay techniques", published in 1987 by Igaku Shoin).

In another aspect, the invention provides a pharmaceutical composition, comprising the monoclonal antibody or antigen binding fragment thereof, or the anti-idiotype antibody according to the invention, and a pharmaceutically acceptable carrier and/or excipient. In some preferred embodiments, the monoclonal antibody is selected from:

(1) a monoclonal antibody, comprising: VH CDR1-3 with amino acid sequences set forth in SEQ ID NO: 1-3, respectively, and/or VL CDR1-3 with amino acid sequences set forth in SEQ ID NO: 4-6, respectively; preferably, comprising: VH set forth in SEQ ID NO: 19 and/or VL set forth in SEQ ID NO: 20; more preferably, a monoclonal antibody produced by Hybridoma cell line 12G6, which has been deposited in China Center for Type Culture Collection (CCTCC), and has a deposition number of CCTCC NO:C201527;

(2) a monoclonal antibody, comprising: VH CDR1-3 with amino acid sequences set forth in SEQ ID NO: 7-9, respectively, and/or VL CDR1-3 with amino acid sequences set forth in SEQ ID NO: 10-12, respectively; preferably, comprising: VH set forth in SEQ ID NO: 21 and/or VL set forth in SEQ ID NO: 22; more preferably, a monoclonal antibody produced by Hybridoma cell line 7G6, which has been deposited in China Center for Type Culture Collection (CCTCC), and has a deposition number of CCTCC NO:C201435; or (3) a monoclonal antibody, comprising: VH CDR1-3 with amino acid sequences set forth in SEQ ID NO: 13-15, respectively, and/or VL CDR1-3 with amino acid sequences set forth in SEQ ID NO: 16-18, respectively; preferably, comprising: VH set forth in SEQ ID NO: 23 and/or VL set forth in SEQ ID NO: 24; more preferably, a monoclonal antibody produced by Hybridoma cell line 11B10, which has been deposited in China Center for Type Culture Collection (CCTCC), and has a deposition number of CCTCC NO:C201432.

In some preferred embodiments, the pharmaceutical composition further an additional pharmaceutically active agent (e.g., an anti-influenza agent, such as an inhibitor of M2 protein ion channel (e.g., amantadine and rimantadine) and a neuraminidase inhibitor (e.g., Oseltamivir)).

In another aspect, the invention provides a method for neutralizing virulence of influenza B virus in a sample, comprising contacting a sample comprising influenza B virus with the monoclonal antibody or antigen binding fragment thereof according to the invention. The method may be used for therapeutic purposes or for non-therapeutic purposes (e.g., the sample is a cell sample, instead of a patient or a sample from a patient). Preferably, the influenza B virus is selected from Yamagata lineage and Victoria lineage of influenza B viruses.

In another aspect, the invention provides use of the monoclonal antibody or antigen binding fragment thereof according to the invention in the manufacture of a pharmaceutical composition for neutralizing the virulence of influenza B virus in a sample. In another aspect, the invention provides the monoclonal antibody or antigen binding fragment thereof as described above, for neutralizing the virulence of influenza B virus in a sample.

In another aspect, the invention provides use of the monoclonal antibody or antigen binding fragment thereof or anti-idiotype antibody according to the invention in the manufacture of a pharmaceutical composition for preventing or treating an infection by influenza B virus or a disease (e.g., influenza) associated with the infection in a subject. In another aspect, the invention provides the monoclonal antibody or antigen binding fragment thereof or the anti-idiotype antibody as described above, for preventing or treating an infection by influenza B virus or a disease (e.g., influenza) associated with the infection in a subject.

In another aspect, the invention provides a method for preventing or treating an infection by influenza B virus or a disease (e.g., influenza) associated with the infection in a subject, comprising administering to a subject in need thereof a prophylactically or therapeutically effective amount of the monoclonal antibody or antigen binding fragment thereof or anti-idiotype antibody according to the invention, or the pharmaceutical composition according to the invention.

In some preferred embodiments, the subject is a mammal, for example, human.

The monoclonal antibody or antigen binding fragment thereof or the anti-idiotype antibody according to the invention or the pharmaceutical composition according to the invention may be administered to a subject by any suitable route. Such routes include, but are not limited to, oral, buccal, sublingual, topical, parenteral, rectal, intravaginal, or rhinal route.

In some preferred embodiments, the monoclonal antibody is such an antibody, comprising: VH CDR1-3 with amino acid sequences set forth in SEQ ID NO: 1-3, respectively, and/or VL CDR1-3 with amino acid sequences set forth in SEQ ID NO: 4-6, respectively; preferably, comprising: VH set forth in SEQ ID NO: 19 and/or VL set forth in SEQ ID NO: 20; more preferably, is the monoclonal antibody 12G6.

In some preferred embodiments, the monoclonal antibody is such an antibody, comprising: VH CDR1-3 with amino acid sequences set forth in SEQ ID NO: 7-9, respectively, and/or VL CDR1-3 with amino acid sequences set forth in SEQ ID NO: 10-12, respectively; preferably, comprising: VH set forth in SEQ ID NO: 21 and/or VL set forth in SEQ ID NO: 22; more preferably, is the monoclonal antibody 7G6.

In some preferred embodiments, the monoclonal antibody is such an antibody, comprising: VH CDR1-3 with amino acid sequences set forth in SEQ ID NO: 13-15, respectively, and/or VL CDR1-3 with amino acid sequences set forth in SEQ ID NO: 16-18, respectively; preferably, comprising: VH set forth in SEQ ID NO: 23 and/or VL set forth in SEQ ID NO: 24; more preferably, is the monoclonal antibody 11B10.

The medicament and the pharmaceutical composition provided in the invention may be used alone or in combination with an additional pharmaceutically active agent (e.g., an anti-influenza agent, such as an inhibitor of M2 protein ion channel (e.g., amantadine and rimantadine) and a neuraminidase inhibitor (e.g., Oseltamivir)).

BENEFICIAL TECHNICAL EFFECTS OF THE INVENTION

Compared with the prior art, the monoclonal antibody and antigen binding fragment thereof according to the invention have significant beneficial effects. In particular, the monoclonal antibody and antigen binding fragment thereof according to the invention can specifically bind to HA protein of at least two lineages (e.g., Yamagata subtype and Victoria subtype) of influenza B viruses, show a broad-spectrum virus-binding reactivity and a broad-spectrum virus-neutralizing ability, and therefore have a particularly significant advantage in preventing or treating an infection by influenza B virus or a disease (e.g., influenza) associated with the infection in a subject.

The embodiments of the invention are illustrated in detail by reference to the following drawings and examples. However, it is understood by those skilled in the art that the following drawings and examples are used only for the purpose of illustrating the invention, rather than limiting the scope of the invention. According to the detailed description of the following drawings and preferred embodiments, various purposes and advantages of the invention are apparent for a person skilled in the art.

DESCRIPTION OF THE DRAWINGS

In FIG. 1A, receptor binding sites of HA are marked in green, and the amino acid sites recognized by the monoclonal antibody 12G6 are marked in red. The results show that the key epitope amino acids recognized by the monoclonal antibody 12G6 are at position 156, position 176 and position 183 of HA. In FIG. 1B, receptor binding sites of HA are marked in green, and the amino acid sites recognized by the monoclonal antibody 7G6 are marked in red. The results show that the key epitope amino acids recognized by the monoclonal antibody 7G6 are at position 156, position 165 and position 180 of HA. In FIG. 1C, receptor binding sites of HA are marked in green, and the amino acid sites recognized by the monoclonal antibody 11B10 are marked in red. The results show that the key epitope amino acid recognized by the monoclonal antibody 11B10 is at position 180 of HA.

Figure 3:
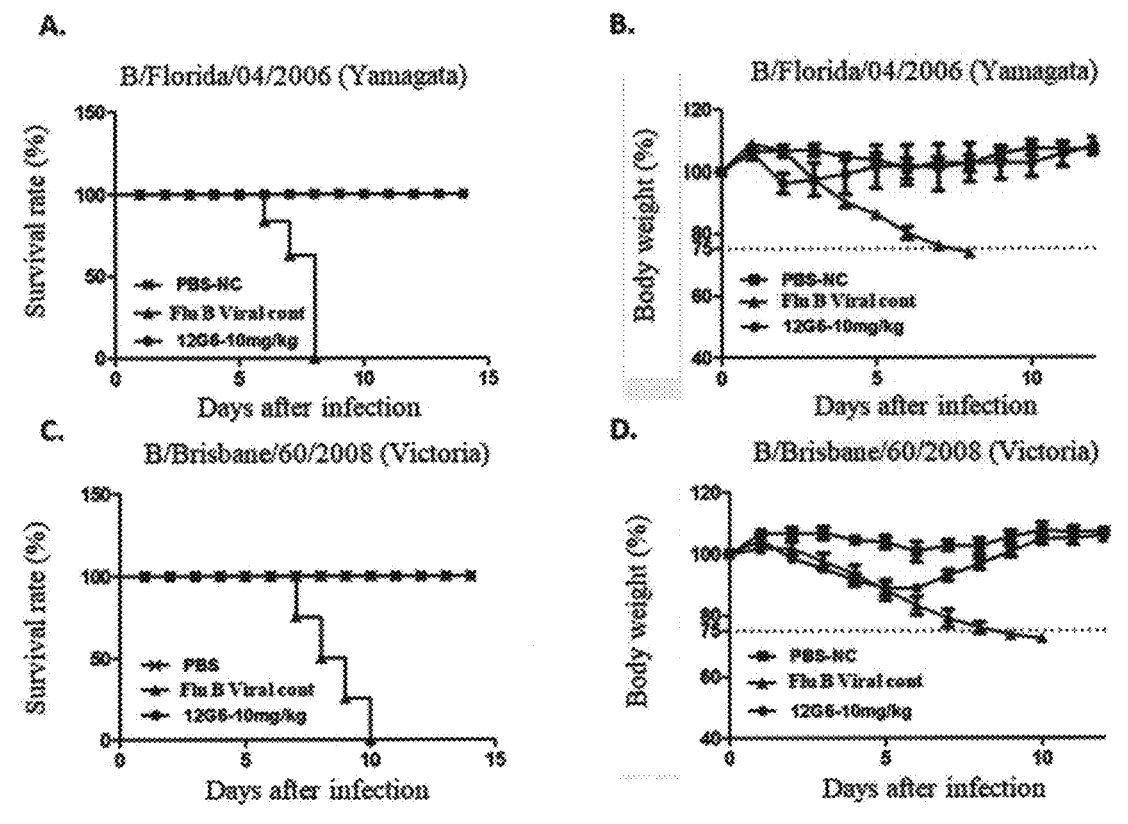

FIG. 3 shows the protective effect of the monoclonal antibody 12G6 in mice infected by influenza B virus B/Florida/04/2006 (FL04-MA) and B/Brisbane/60/2008 (BR60-MA).

FIG. 3A and FIG. 3B show changes in survival rate and body weight of mice in negative control group (PBS-NC), B/Florida/04/2006 virus-infected control group (Flu B Viral cont) and therapeutic group (12G6-10 mg/kg), respectively. FIG. 3C and FIG. 3D show changes in survival rate and body weight of mice in negative control group (PBS-NC), B/Brisbane/60/2008 virus-infected control group (Flu B Viral cont) and therapeutic group (12G6-10 mg/kg), respectively.

The results show that no significant weight fluctuation was observed in the mice in the negative control group during the whole experiment, while significant weight loss was observed in the mice in the two virus-infected control groups. All the mice in the B/Florida/04/2006 virus control group died 8 days after infection, and all the mice in the B/Brisbane/60/2008 virus control group died 10 days after infection. For the two influenza B viruses, the intervention by injection of the antibody 12G6 at a dose of 10 mg/kg can enable the infected mice to regain the body weight, and enable the infected mice to survive normally for 14 days, with a treatment effectiveness of 100%.

Figure 4:
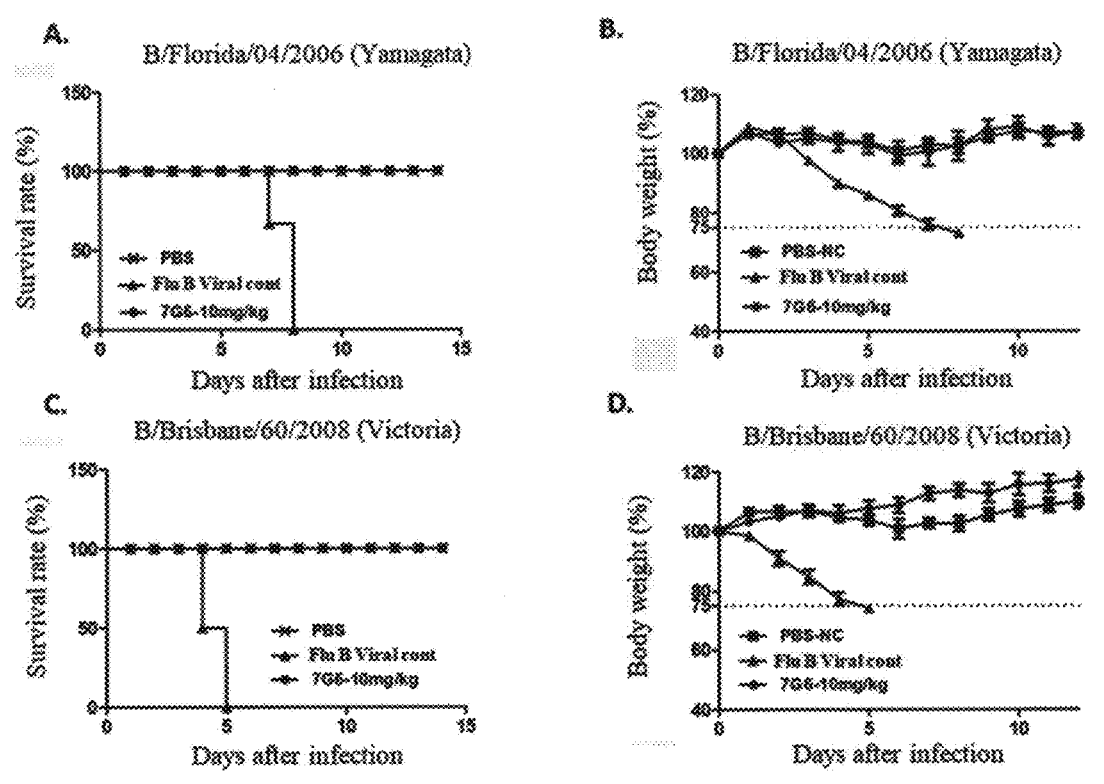

FIG. 4 shows the protective effect of the monoclonal antibody 7G6 in mice infected by influenza B virus B/Florida/04/2006 (FL04-MA) and B/Brisbane/60/2008 (BR60-MA).

FIG. 4A and FIG. 4B show changes in survival rate and body weight of mice in negative control group (PBS-NC), B/Florida/04/2006 virus-infected control group (Flu B Viral cont) and therapeutic group (7G6-10 mg/kg), respectively. FIG. 4C and FIG. 4D show changes in survival rate and body weight of mice in negative control group (PBS-NC), B/Brisbane/60/2008 virus-infected control group (Flu B Viral cont) and therapeutic group (7G6-10 mg/kg), respectively.

The results show that no significant weight fluctuation was observed in the mice in the negative control group during the whole experiment, while significant weight loss was observed in the mice in the two virus-infected control groups. All the mice in the B/Florida/04/2006 virus control group died 8 days after infection, and all the mice in the B/Brisbane/60/2008 virus control group died 5 days after infection. For the two influenza B viruses, the intervention by injection of the antibody 7G6 at a dose of 10 mg/kg can enable the infected mice to regain the body weight, and enable the infected mice to survive normally for 14 days, with a treatment effectiveness of 100%.

Figure 5:
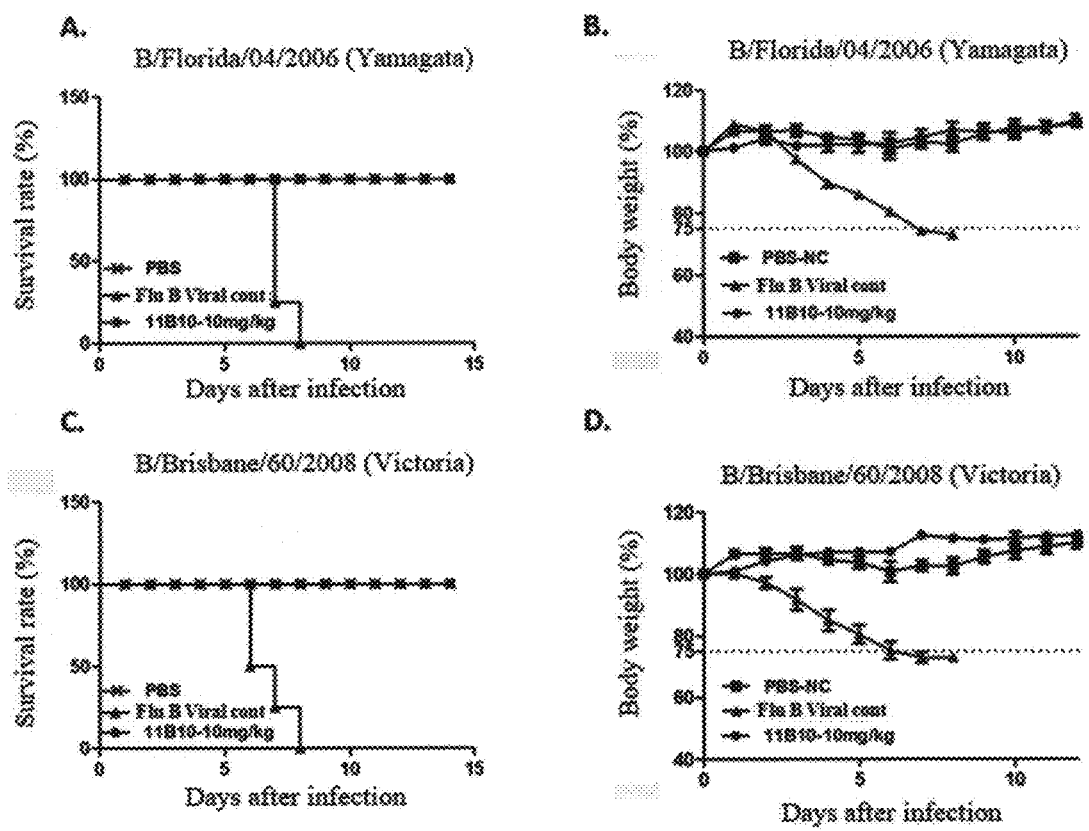

FIG. 5 shows the protective effect of the monoclonal antibody 11B10 in mice infected by influenza B virus B/Florida/04/2006 (FL04-MA) and B/Brisbane/60/2008 (BR60-MA).

FIG. 5A and FIG. 5B show changes in survival rate and body weight of mice in negative control group (PBS-NC), B/Florida/04/2006 virus-infected control group (Flu B Viral cont) and therapeutic group (11B10-10 mg/kg), respectively. FIG. 5C and FIG. 5D show changes in survival rate and body weight of mice in negative control group (PBS-NC), B/Brisbane/60/2008 virus-infected control group (Flu B Viral cont) and therapeutic group (11B10-10 mg/kg), respectively.

The results show that no significant weight fluctuation was observed in the mice in the negative control group during the whole experiment, while significant weight loss was observed in the mice in the two virus-infected control groups. All the mice in the B/Florida/04/2006 virus control group died 8 days after infection, and all the mice in the B/Brisbane/60/2008 virus control group died 8 days after infection. For the two influenza B viruses, the intervention by injection of the antibody 11B10 at a dose of 10 mg/kg can enable the infected mice to regain the body weight, and enable the infected mice to survive normally for 14 days, with a treatment effectiveness of 100%.

Figures 6, 7:
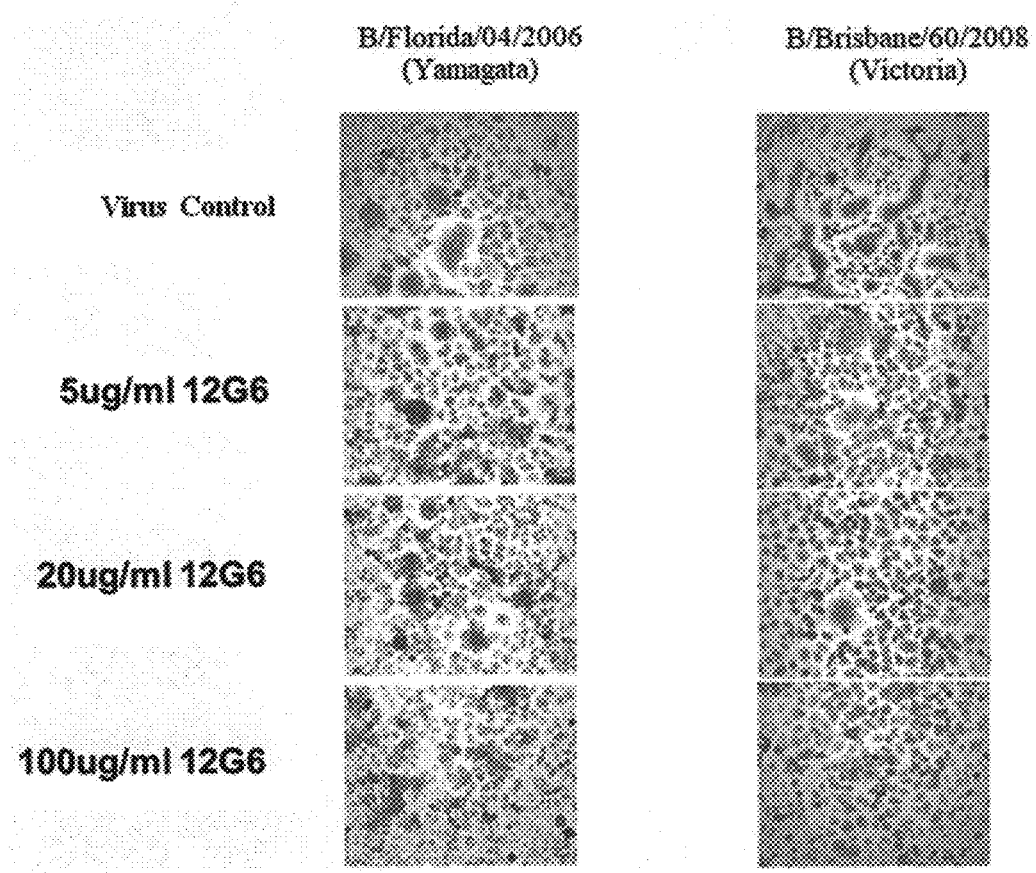

FIG. 6 shows the immunofluorescence analysis results of MDCK cells infected by influenza B virus B/Florida/04/2006 (Yamagata) or B/Brisbane/60/2008 (Victoria), wherein, prior to being used to infect MDCK cells, the influenza B virus was incubated with the monoclonal antibody 12G6, a polyclonal antiserum against B/Florida/4/2006 virus (B/FL. antiserum), a polyclonal antiserum against B/Malaysia/2506/2004 virus (B/Mal. antiserum) or PBS (an antibody-free control), respectively.

FIG. 7 shows the results on the staining of MDCK cells infected by influenza B virus B/Florida/4/2006 (Yamagata) or B/Brisbane/60/2008 (Victoria) with Giemsa Stain, wherein after infection with the virus, the MDCK cells were incubated with the antibody 12G6 at 0 µg/ml, 5 µg/ml, 20 µg/ml or 100 µg/ml.

Figure 8:
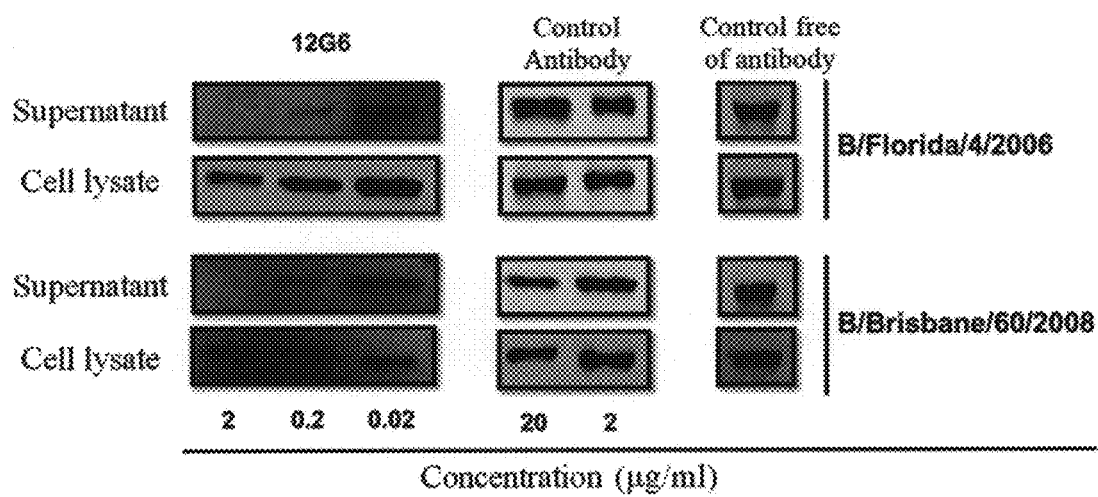

FIG. 8 shows the results of immunoblotting assay for detecting NP protein in the culture supernatant and cell lysate of MDCK cells, wherein the MDCK cells were infected with influenza B virus B/Florida/4/2006 (Yamagata) or B/Brisbane/60/2008 (Victoria), and after the infection, were incubated in a culture medium (a control free of antibody) or with a given concentration of the monoclonal antibody 12G6 (2 µg/ml, 0.2n/ml or 0.02 µg/ml; diluted in the culture medium) or a given concentration of a negative control antibody (20 µg/ml or 2 µg/ml; diluted in the culture medium).

Figure 9:
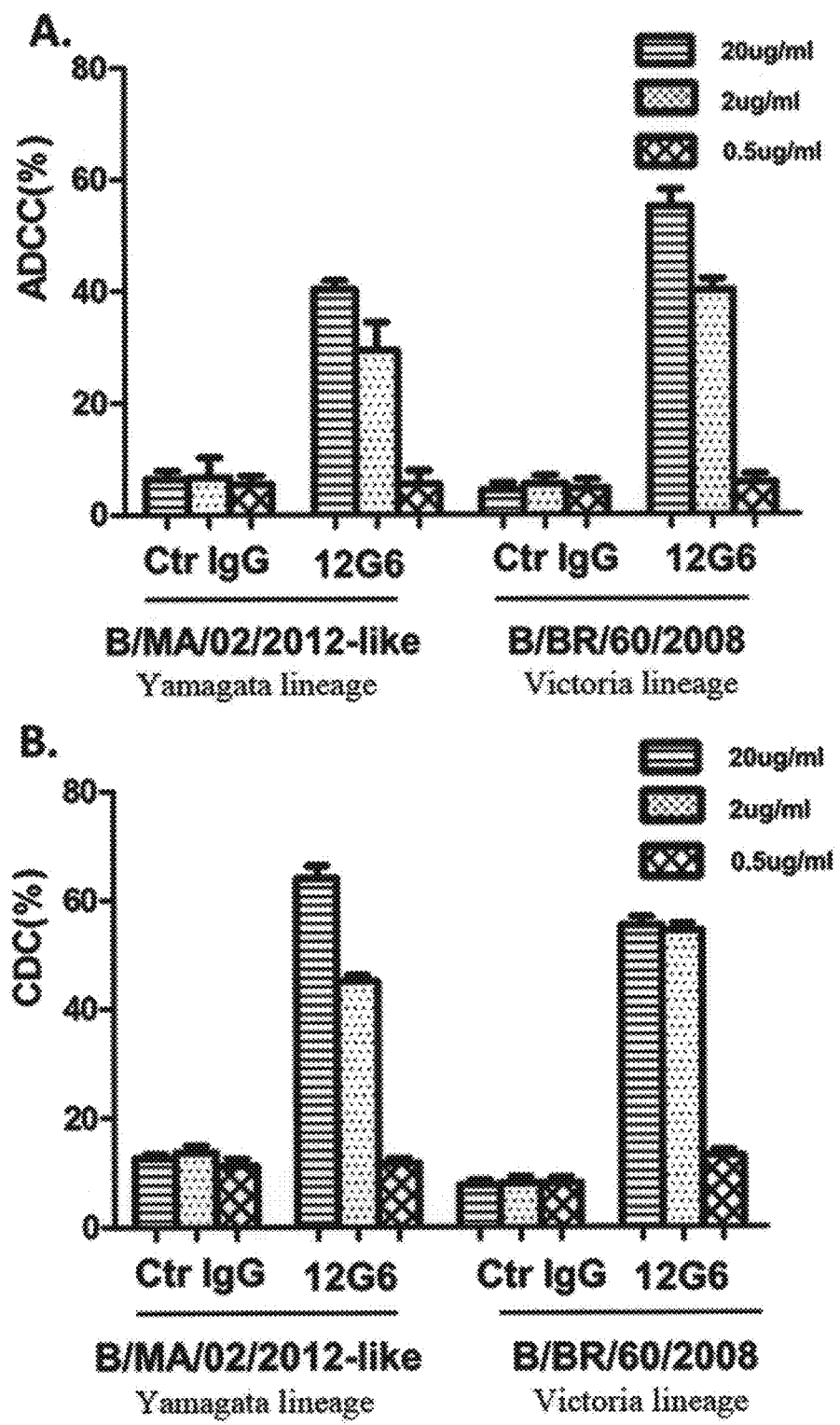

FIG. 9 shows the analytic results of ADCC (FIG. 9A) and CDC (FIG. 9B) against influenza virus Massachusetts/02/2012-like (Yamagata) and B/Brisbane/60/2008 (Victoria) triggered by the monoclonal antibody 12G6 and the negative control antibody; wherein Ctr: negative control antibody (anti-HIV mAb 5G6).

Sequence Information

Information of the sequences involved in the invention is provided in the following Table 1.

TABLE 1

| SEQ ID NO: | Sequence depiction |
|---|---|
| 1 | the amino acid sequence of heavy chain CDR1 of 12G6<br>GYTFTDYY |
| 2 | the amino acid sequence of heavy chain CDR2 of 12G6<br>VNPYSGGT |
| 3 | the amino acid sequence of heavy chain CDR3 of 12G6<br>ARWDYGVYEGYIDY |
| 4 | the amino acid sequence of light chain CDR1 of 12G6<br>EKIYSN |
| 5 | the amino acid sequence of light chain CDR2 of 12G6<br>AAI |
| 6 | the amino acid sequence of light chain CDR3 of 12G6<br>QHFWGTPLT |
| 7 | the amino acid sequence of heavy chain CDR1 of 7G6<br>GYTFTDYN |
| 8 | the amino acid sequence of heavy chain CDR2 of 7G6<br>IYPNNGGT |
| 9 | the amino acid sequence of heavy chain CDR3 of 7G6<br>VRSGAYYFNYLVPYFDY |
| 10 | the amino acid sequence of light chain CDR1 of 7G6<br>ESVDIYGNSF |
| 11 | the amino acid sequence of light chain CDR2 of 7G6<br>LAS |
| 12 | the amino acid sequence of light chain CDR3 of 7G6<br>QQNYEDPWT |
| 13 | the amino acid sequence of heavy chain CDRI of 11B10<br>GYTFTGYN |
| 14 | the amino acid sequence of heavy chain CDR2 of 11B10<br>IYPNNGVT |
| 15 | the amino acid sequence of heavy chain CDR3 of 11B10<br>VRSGAYYVNYLVPYFDY |

TABLE 1-continued

| SEQ ID NO: | Sequence depiction |
|---|---|
| 16 | the amino acid sequence of light chain CDR1 of 11B10<br>ESIDIYGNSF |
| 17 | the amino acid sequence of light chain CDR2 of 11B10<br>RAS |
| 18 | the amino acid sequence of light chain CDR3 of 11B10<br>QQNYEDPWT |
| 19 | the amino acid sequence of heavy chain variable region (VH) of 12G6<br>EVHLQQSGPELVKPGASVKMSCEASGYTFTDYYVAWVKQSPGESFEWIGRVNPYS<br>GGTSYNQKFKGKATLIVDKSSSTAYMELSSLTSEDSAVYYCARWDYGVYEGYIDY<br>WGQGSALTV |
| 20 | the amino acid sequence of light chain variable region (VL) of 12G6<br>DIQMTQSPASLSVSVGETVTITCRASEKIYSNLAWYQQKEGKSPQLLVYAAIRLAD<br>GVPSRFSGSGSGTQFSLKINSLQSEDFGTYYCQHFWGTPLTFGAGTKLELK |
| 21 | the amino acid sequence of heavy chain variable region (VH) of 7G6<br>EVQLQQSGPELVKPGASVKISCKASGYTFTDYNMHWVKQSLGKSLEWIGYIYPNN<br>GGTGYNQKFESKATLTVDNSSSTAYMELRTLTSEDSAVYYCVRSGAYYFNYLVPY<br>FDYWGQGTTLTVSS |
| 22 | the amino acid sequence of light chain variable region (VL) of 7G6<br>NIVLTQSPASLAVSLGQRATISCRASESVDIYGNSFMHWYQQKPGQPPKWYLASK<br>LECGVCARFNGSGCRTDFTLAIDPVEGDDGATYYCQQNYEDPWTFGGGTKLEIK |
| 23 | the amino acid sequence of heavy chain variable region (VH) of 11B10<br>EVQLQQSGPELVKPGASVKISCKASGYTFTGYNMHWVKQSHGKSLEWIGKIYPNN<br>GVTGYNQEFRSKATLTVDNSSSTAYMELRSLTSEDSAIYFCVRSGAYYVNYLVPYF<br>DYWGQGTTLTVSS |
| 24 | the amino acid sequence of light chain variable region (VL) of 11B10<br>NIVLTQSPASLAVSPGQRATISCRASESIDIYGNSFM+56IWYQKKPGQPPKLLIYRASNL<br>ESGVPARFNGSGSRTDFTLTIDPVEGDDGATYYCQQNYEDPWTFGGGTKLEIK |
| 25 | the nucleotide sequence encoding the heavy chain variable region (VH) of 12G6<br>GAGGTCCACCTGCAACAGTCTGGACCTGAGCTGGTGAAGCCTGGGGCTTCAGTG<br>AAGATGTCCTGTGAGGCTTCTGGATACACATTCACTGACTACTACGTGGCCTGG<br>GTGAAGCAGAGCCCTGGAGAAAGCTTTGAGTGGATTGGACGTGTTAATCCTTAC<br>AGTGGTGGTACTAGTTACAACCAGAAGTTCAAGGGCAAGGCCACATTGATTGTT<br>GACAAGTCCTCCAGCACAGCCTACATGGAGCTCAGCAGCCTGACATCTGAGGA<br>CTCTGCGGTCTATTACTGTGCTAGATGGGACTATGGTGTCTACGAGGGGTACAT<br>TGACTACTGGGGCCAAGGCTCCGCTCTCACAGTC |
| 26 | the nucleotide sequence encoding the light chain variable region (VL) of 12G6<br>GACATCCAGATGACTCAGTCTCCAGCCTCCCTATCTGTATCTGTGGGAGAAACT<br>GTCACCATCACATGTCGAGCAAGTGAGAAAATTTACAGTAATTTAGCATGGTAT<br>CAGCAGAAAGAGGGAAAATCTCCTCAGCTCCTGGTCTATGCTGCAATAAGATTA<br>GCAGATGGTGTGCCATCAAGGTTCAGTGGCAGTGGATCAGGCACACAGTTTTCC<br>CTCAAGATCAACAGCCTGCAGTCTGAAGATTTTGGGACTTATTACTGTCAACAT<br>TTTTGGGGTACTCCTCTCACGTTCGGTGCTGGGACCAAGCTGGAGCTGAAA |
| 27 | the nucleotide sequence encoding the heavy chain variable region (VH) of 7G6<br>GAGGTCCAGCTTCAGCAGTCAGGACCTGAGCTGGTGAAACCTGGGGCCTCAGT<br>GAAGATATCCTGCAAGGCTTCTGGATACACATTCACTGACTACAACATGCACTG<br>GGTGAAGCAGAGCCTTGGAAAGAGCCTTGAGTGGATTGGATATATTTATCCTAA<br>CAATGGTGGTACTGGCTACAATCAGAAGTTCGAGAGTAAGGCCACATTGACTGT<br>AGACAATTCCTCCAGCACAGCCTACATGGAGCTCCGCACCCTGACATCTGAGGA<br>CTCTGCAGTCTATTACTGTGTAAGATCAGGAGCCTACTATTTTAACTACCTAGTC<br>CCCTACTTTGACTACTGGGGCCAAGGCACCACTCTCACAGTCTCCTCA |
| 28 | the nucleotide sequence encoding the light chain variable region (VL) of 7G6<br>AACATTGTGCTGACCCAATCTCCAGCTTCTTTGGCTGTGTCTCTAGGGCAGAGG<br>GCCACCATATCTTGCAGAGCCAGTGAAAGTGTTGATATTTATGGCAATAGTTTT<br>ATGCACTGGTACCAGCAGAAACCAGGACAGCCACCCAAACTCCTCATTTATCTT<br>GCATCCAAACTAGAATGTGGGGTGTGTGCCAGGTTCAATGGCAGTGGGTGTAG<br>GACAGACTTCACCCTCGCTATTGATCCTGTGGAGGGTGATGATGGTGCAACCTA<br>TTACTGTCAGCAAAATTATGAGGATCCGTGGACGTTCGGTGGAGGCACCAAGCT<br>GGAAATCAAA |
| 29 | the nucleotide sequence encoding the heavy chain variable region (VH) of 11B10<br>GAGGTCCAGCTTCAGCAGTCAGGACCTGAGCTGGTGAAACCTGGGGCCTCAGT<br>GAAGATATCCTGCAAGGCTTCTGGATACACATTCACTGGCTACAACATGCACTG<br>GGTGAAGCAGAGCCATGGAAAGAGCCTTGAGTGGATTGGAAAAATTTATCCTA<br>ACAATGGTGTTACTGGCTACAACCAGGAGTTCAGGAGCAAGGCCACATTGACT<br>GTAGACAATTCCTCCAGCACAGCCTACATGGAGCTCCGCAGCCTGACATCTGAG |

TABLE 1-continued

| SEQ ID NO: | Sequence depiction |
|---|---|
| | GACTCTGCAATCTATTTCTGTGTAAGATCAGGAGCCTACTATGTTAACTACCTA<br>GTCCCCTACTTTGACTACTGGGGCCAAGGCACCACTCTCACAGTTTCCTCA |
| 30 | the nucleotide sequence encoding the light chain variable region (VL) of 11B10<br>AACATTGTGCTGACCCAATCTCCAGCCTCTTTGGCTGTGTCTCCAGGGCAGAGG<br>GCCACCATATCCTGCAGAGCCAGTGAAAGTATTGATATTTATGGCAATAGTTTT<br>ATGCACTGGTACCAGAAGAAACCAGGACAGCCACCCAAACTCCTCATTTATCGT<br>GCATCCAACCTAGAATCTGGGGTCCCTGCCAGGTTCAATGGCAGTGGGTCTAGG<br>ACAGACTTCACCCTCACCATTGATCCTGTGGAGGGTGATGATGGTGCAACCTAT<br>TACTGTCAACAAAATTATGAGGATCCGTGGACGTTCGGTGGAGGTACCAAGCTG<br>GAAATCAAA |
| 31 | primer MVJkR<br>5'-CCG TTT GKA TYT CCA GCT TGG TSC C-3' |
| 32 | primer MVDJhR<br>5'-CGG TGA CCG WGG TBC CTT GRC CCC A-3' |
| 33 | primer 12G6VhMuIgVh5'-B2<br>5'-ATGGACTCCAGGCTCAATTTAGTTTTCCT-3' |
| 34 | primer 12G6Vk MuIgkV15'-F4<br>5'-ATGAAGTTGCCTGTTAGGCTGTTGGTGCT-3' |
| 35 | primer 7G6Vh MuIgVh5'-B2<br>5'-ATGGACTCCAGGCTCAATTTAGTTTTCCT-3' |
| 36 | primer 7G6Vk MuIgkV15'-B<br>5'-ATGGAGACAGACACACTCCTGCTAT-3' |
| 37 | primer 11B10VhMuIgVh5'B1<br>5'-ATGRAATGSASCTGGGTYWTYCTCTT-3' |
| 38 | primer 11B10VkMuIgkV15'-G2<br>5'-ATGGTYCTYATVTCCTTGCTGTTCTGG-3' |
| 39 | the amino acid sequence of HA protein of B/Xiamen/1346/2008 (Victoria lineage)<br>MVVTSNADRICTGITSSNSPHVVKTATQGEVNVTGVIPLTTTPTKSHFANLKGTETR<br>GKLCPKCLNCTDLDVALGRPKCTGNIPSARVSILHEVRPVTSGCFPIMHDRTKIRQL<br>PNLLRGYEHIRLSTHNVINAENAPGGPYKIGTSGSCPNVTNGNGFFATMAWAVPKN<br>DNNKTATNSLTIEVPYICTEGEDQITVWGFHSDNETQMAKLYGDSKPQKFTSSANG<br>VTTHYVSQIGGFPNQTEDGGLPQSGRIVVDYMVQKSGKTGTITYQRGILLPQKVWC<br>ASGKSKVIKGSLPLIGEADCLHEKYGGLNKSKPYYTGEHAKAIGNCPIWVKTPLKL<br>ANGTKYRPPAKLLKERGFFGAIAGFLEGGWEGMIAGWHGYTSHGAHGVAVAADL<br>KSTQEAINKITKNLNSLSELEVKNLQRLSGAMDELHNEILELDEKVDDLRADTISSQI<br>ELAVLLSNEGIINSEDEHLLALERKLKKMLGPSAVEIGNGCFETKHKCNQTCLDRIA<br>AGTFDAGEFSLPTFDSLNITAASLNDDGLDNHTILLYYSTAASSLAVTLMIAIFVVY<br>MVSRDNVSCFHS |
| 40 | the amino acid sequence of HA protein of B/Singapore/3/1964<br>MVVTSNADRICTGITSSNSPHVVKTATQGEVNVTGVIPLTTTPTKSHFANLKGTQTR<br>GKLCPNCLNCTDLDVALGRPKCMGTIPSAKASILHEVKPVTSGCFPIMHDRTKIRQL<br>PNLLRGYENIRLSARNVINAETAPGGPYIVGTSGSCPNVTNGKGFFATMAWAVPKN<br>KNKTATNPLTVEVPYICTKGEDQITVWGFHSDNEAQMVTLYGDSKPQKFTSSANG<br>VTTHYVSQIGGFPNQTEDEGLQQSGRIVVDYMVQKPGKTGTIVYQRGVLLPQKVW<br>CASGRSKVIKGSLPLIGEADCLHEKYGGLNKSKPYYTGEHAKAIGNCPIWVKTPLK<br>LANGTKYRPPAKLLKERGFFGAIAGFLEGGWEGMIAGWHGYTSHGAHGVAVAAD<br>LKSTQEAINKITKNLNSLSELEVKNLQRLSGAMDELHNEILELDEKVDDLRADTISS<br>QIELAVLLSNEGIINSEDEHILLALERKLKKMLGPSAVDIGNGCFETKIIKCNQTCLDR<br>IAAGTFNAGEFSLPTEDSLNITAASLNDDGLDNHTILLYYSTAASSLAVTLMIAIFIV<br>YMVSRDNVFLLHLSIRK |

Description of Deposition of Biological Materials

The invention relates to the following biological materials deposited in China Center for Type Culture Collection (CCTCC, Wuhan University, Wuhan, China):

Hybridoma cell line 12G6, with a deposition number of CCTCC NO: C201527, deposited on Apr. 10, 2015;

Hybridoma cell line 7G6, with a deposition number of CCTCC NO: C201435, deposited on Mar. 26, 2014; and Hybridoma cell line 11B10, with a deposition number of CCTCC NO: C201432, deposited on Mar. 26, 2014.

SPECIFIC MODES FOR CARRYING OUT THE INVENTION

The present invention is illustrated by reference to the following examples (which are not intended to limit the scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. In the case where the concrete conditions are not indicated in the examples, the examples are carried out according to conventional conditions or the conditions recommended by the manufacturer. The reagents or apparatuses, the manufacturers of which are not indicated, are conventional products that are commercially available. Those skilled in the art understand that the examples are used for illustrating the present invention, but not intended to limit the scope of the present invention.

Example 1: Preparation of Monoclonal Antibodies Against HA Protein of Influenza B Virus 1. Preparation of Virus Antigen MDCK cells were inoculated with four strains of influenza B virus, i.e., B/Xiamen/891/2006 (Yamagata), B/Xiamen/1346/2008 (Victoria), B/Xiamen/N697/2012 (Yamagata), and B/Xiamen/3043/2006 (Victoria), respectively. After incubating the cells at 37° C. for 2 days, the supernatant was collected to get the amplified viruses. Live viruses were collected, and were inactivated with 0.03% formalin at 4° C. The inactivated viruses were subjected to HA titration to determine the titer of the inactivated viruses (Note: please refer to WHO Operation Guideline for the particular steps of HA titration). B/Xiamen/891/2006 (Yamagata), B/Xiamen/1346/2008 (Victoria), B/Xiamen/N697/2012 (Yamagata), and B/Xiamen/3043/2006 (Victoria) were strains of influenza B virus isolated in the inventor's laboratory.

2. Experimental Mice:

6-Week old, SPF-grade female Balb/C mice were provided by Experimental Animal Center, Xiamen University.

3. Preparation of Hybridoma:

Hybridoma cells secreting monoclonal antibodies were obtained by standard in vivo immunization method and PEG fusion method; please refer to Ed Harlow et al., "Antibodies A Laboratory Manual", Cold Spring Harbor Laboratory 1988 for detail. The brief process was as followed.

3.1 Immunization of Mice:

The titers of the inactivated viruses were adjusted to 128HA, and then the mice were immunized by means of sequential immunization. In brief, firstly, the virus B/Xiamen/891/2006 (Yamagata) was mixed and emulsified with an equal volume of Freund's complete adjuvant (CFA), and then was administered to limbs of mice by multi-point intramuscular injection for primary immunization, at an amount of 400 ul for each mouse. The viruses B/Xiamen/1346/2008 (Victoria), B/Xiamen/N697/2012 (Yamagata), and B/Xiamen/3043/2006 (Victoria) were separately mixed and emulsified with incomplete Freund's adjuvant (IFA), and then administered to the mice for booster immunization at 14 d, 28 d and 42 d after the primary immunization, respectively. Finally, the booster immunization was performed to the spleens of mice at 56 d after the primary immunization, wherein the immunogen was a mixture of the above virus solutions mixed at an equal volume 100 ul for each mouse. 3 d after the immunization, spleens of the mice were taken for fusion experiment.

3.2 Cell Fusion:

The spleen was ground to obtain a suspension of spleen cells, and then was mixed with mouse myeloma cells SP2/0 in exponential growth phase. Cell fusion was carried out in the presence of PEG1500. The fused cells were re-suspended in 400 ml fusion culture medium, and then were seeded to 20 96-well plates for culture. The fusion culture medium was a RPMI1640 complete screening culture medium containing HAT and 20% FBS.

3.3 Screening of Hybridoma:

After culturing the fused cells in the 96-well plates for 10 days, the cell supernatant was taken for Hemagglutination-Inhibition (HI) assay and ELISA. The viruses for detection were B/Xiamen/891/2006 (Yamagata) and B/Xiamen/1346/2008 (Victoria). For HI assay, the antibodies secreted in the positive wells should be able to inhibit the agglutination of influenza B virus and red blood cell; for ELISA, the antibodies secreted in the positive wells should be able to specifically react with the influenza B virus coated onto the polystyrene plate. The positive clones as screened were subjected to cloning for three times, so as to obtain hybridoma cell lines capable of stably secreting antibodies. Finally, 41 hybridoma cells lines against HA protein of influenza B virus, including 12G6, 7G6, and 11B10, were obtained.

3.4 Culture of Hybridoma:

41 Stable hybridoma cell lines were subjected to amplification culture in a $CO_2$ incubator, and then were transferred from a 96-well plate to a 24-well plate, and later to a 50 ml cell bottle for further culture. Then, the cells collected from the cell bottle were injected to peritoneal cavities of mice. 7-10 d later, ascites containing monoclonal antibodies were drawn from the peritoneal cavities of mice.

4. Purification of Monoclonal Antibodies

The ascites containing monoclonal antibodies were precipitated with a 50% ammonium sulfate solution. The precipitate obtained was then dissolved in PBS, and then purified through Protein A column in AKTA system to get the purified monoclonal antibodies. The purity of the purified monoclonal antibodies was identified by SDS-PAGE.

Example 2: Identification of Broad-Spectrum Monoclonal Antibodies Recognizing HA Protein of Different HA Lineages of Influenza B Virus Representative stains of influenza B virus, which were isolated at different times from different regions and represented different variant types, and representative stains of influenza A virus as control, were selected. HI assay was used to determine the cross-reactivity of said 41 monoclonal antibodies with different lineages of influenza B virus variant strains. Please refer to WHO Operation Guideline for the HI assay. According to the reactivity of the monoclonal antibodies with the influenza virus strains, three broad-spectrum monoclonal antibodies 12G6, 7G6 and 11B10, which could recognize Yamagata and Victoria lineages of influenza B virus simultaneously (i.e., recognize HA protein of different HA lineages of influenza B virus), were identified (Table 2).

The monoclonal antibodies 12G6, 7G6 and 11B10 could specifically react with Yamagata lineage of influenza B virus and Victoria lineage of influenza B virus, and showed a good broad-spectrum reactivity with different HA lineages. The monoclonal antibody 7G6 could react with unlineaged influenza B viruses discovered at an early stage, Yamagata lineage of influenza B virus and Victoria lineage of influenza B virus. Among all the influenza B viruses used in the assay, the monoclonal antibody 7G6 could react with all of them except for the two virus strains, i.e., B/Harbin/7/1994 (Yamagata lineage) and B/Great Lakes/1739/1954, showing a very broad reactive spectrum.

The monoclonal antibodies 12G6 and 11B10 could specifically react with a part of unlineaged influenza B viruses discovered at an early stage, a part of Yamagata lineage of influenza B viruses and a part of Victoria lineage of influenza B viruses. The monoclonal antibody 11B10 had a broader reactivity spectrum than the monoclonal antibody 12G6 in the case of Yamagata lineage and Victoria lineage of viruses; while the monoclonal antibody 12G6 had a broader reactivity spectrum than the monoclonal antibody 11B10 in the case of the unlineaged influenza B viruses discovered at an early stage.

The results showed that although the monoclonal antibodies 12G6, 7G6 and 11B10 were slightly different in terms of the reactivity with some virus strains, all of them are broad-spectrum monoclonal antibodies having specificity for recognizing different HA lineages of influenza B viruses.

TABLE 2

Activity of monoclonal antibodies 12G6, 7G6 and 11B10 in HI assay (HI titer)

| HA Lineage | Virus | HI titer of mAbs | | |
|---|---|---|---|---|
| | | 12G6 | 7G6 | 11B10 |
| Unlineaged influenza B viruses discovered at an early stage | B/Lee/1940 | 6400 | 1600 | ≤100 |
| | B/Great Lakes/1739/1954 | 1600 | ≤100 | ≤100 |
| | B/Maryland/1/1959 | ≤100 | 6400 | ≤100 |
| | B/Taiwan/2/1962 | ≤100 | 12800 | 800 |
| | B/Singapore/3/1964 | 400 | 3200 | ≤100 |
| Yamagata lineage | B/Harbin/7/1994 | 200 | ≤100 | ≤100 |
| | B/Florida/4/2006 | 12800 | ≥25600 | 400 |
| | B/Xiamen/891/206 | ≤100 | ≥25600 | 800 |
| | B/Xiamen/756/2007 | ≤100 | 12800 | 400 |
| | B/Xiamen/1147/2008 | ≤100 | ≥25600 | 800 |
| | B/Xiamen/N697/2012 | ≤100 | ≥25600 | 800 |
| Victoria lineage | B/Hong Kong/330/2001 | 3200 | ≥25600 | 800 |
| | B/Malaysia/2506/2004 | 3200 | 6400 | 3200 |
| | B/Xiamen/3043/2006 | ≤100 | 12800 | 6400 |
| | B/Xiamen/165/2007 | ≤100 | 12800 | 3200 |
| | B/Brisbane/60/2008 | 3200 | 3200 | ≤100 |
| | B/Brisbane/33/2008 | 3200 | 3200 | ≤100 |
| | B/Xiamen/1346/2008 | ≤100 | 6400 | 3200 |
| | B/Xiamen/N639/2010 | ≤100 | 3200 | 400 |
| | B/Xiamen/N678/2012 | ≤100 | 6400 | 400 |
| Seasonal H3N2 | A/Brisbane/10/2007 | ≤100 | ≤100 | ≤100 |

Note:
HI titer refers to the maximum dilution fold at which the monoclonal antibody can completely inhibit HA activity of virus; wherein ≤100 means no reactivity.

Example 3. Analysis on Neutralizing Activity of Monoclonal Antibodies 12G6, 7G6 and 11B10

Neutralization activity/titer is an important index for assessing whether a monoclonal antibody has a potential of preventing and treating a disease. In the Example, microwell neutralization assay was used to determine the neutralization activity of the monoclonal antibodies 12G6, 7G6 and 11B10 against the representative strains of different lineages of influenza B viruses (please refer to Hulse-Post et al., PNAS. 2005, 102: 10682-7 for the method). The experimental results were shown in Table 3. Three monoclonal antibodies (12G6, 7G6 and 11B10) had broad-spectrum cross-neutralizing activity for unlineaged influenza B virus discovered at an early stage, Yamagata lineage of influenza B virus and Victoria lineage of influenza B virus. The neutralizing activity of the monoclonal antibody 7G6 was substantively consistent with the HI activity. The monoclonal antibody 7G6 had neutralizing activity for all the tested influenza B viruses except for the two viruses, i.e., B/Harbin/7/1994 (Yamagata lineage) and B/Great Lakes/1739/1954, and showed a relatively broad neutralizing activity spectrum and a very strong reactivity. The neutralizing activity spectrum of the monoclonal antibody 11B10 was slightly broader than the HI activity spectrum. In particular, the monoclonal antibody 11B10 could neutralize almost all the influenza B viruses (except for B/Harbin/7/1994) during 1962-2012. The neutralizing activity spectrum of the monoclonal antibody 12G6 was quite different from the HI activity spectrum, and the monoclonal antibody 12G6 could neutralize all the influenza B viruses during 1940-2012, and showed a very strong and very broad-spectrum neutralizing activity.

TABLE 3

Activity of monoclonal antibodies 12G6, 7G6 and 11B10 in neutralization assay

| Lineage | Virus | Neutralization titer of mAbs | | |
|---|---|---|---|---|
| | | 12G6 | 7G6 | 11B10 |
| Unlineaged influenza B virus discovered at an early stage | B/Lee/1940 | 6400 | 1600 | ≤100 |
| | B/Great Lakes/1739/1954 | ≥25600 | ≤100 | ≤100 |
| | B/Maryland/1/1959 | 3200 | 800 | ≤100 |
| | B/Taiwan/2/1962 | 1600 | 12800 | 800 |
| | B/Singapore/3/1964 | 6400 | ≥25600 | 800 |
| Yamagata lineage | B/Harbin/7/1994 | 3200 | ≤100 | ≤100 |
| | B/Florida/4/2006 | ≥25600 | ≥25600 | 6400 |
| | B/Xiamen/891/206 | 1600 | ≥25600 | 800 |
| | B/Xiamen/756/2007 | 1600 | 12800 | 400 |
| | B/Xiamen/1147/2008 | 1600 | ≥25600 | 800 |
| | B/Xiamen/N697/2012 | 800 | ≥25600 | 800 |
| Victoria lineage | B/Hong Kong/330/2001 | ≥25600 | ≥25600 | ≥25600 |
| | B/Malaysia/2506/2004 | 12800 | ≥25600 | ≥25600 |
| | B/Xiamen/3043/2006 | 3200 | 12800 | 6400 |
| | B/Xiamen/165/2007 | 6400 | 12800 | 3200 |
| | B/Brisbane/60/2008 | ≥25600 | 12800 | 3200 |
| | B/Brisbane/33/2008 | ≥25600 | ≥25600 | 800 |
| | B/Xiamen/1346/2008 | 3200 | 6400 | 3200 |
| | B/Xiamen/N639/2010 | 3200 | 3200 | 400 |
| | B/Xiamen/N678/2012 | 1600 | 6400 | 400 |
| Seasonal H3N2 | A/Brisbane/10/2007 | ≤100 | ≤100 | ≤100 |

Note:
≤100, means no reactivity.

Example 4. Identification of Key Epitope Amino Acids of Monoclonal Antibodies 12G6, 7G6 and 11B10

In the Example, monoclonal antibodies 12G6, 7G6 and 11B10 were used to induce and screen influenza B virus strains having escape mutations. The screened escape viruses were subjected to plaque-purification, amplification culture, gene retrieve, sequencing, and structural localization of escape mutation sites, so as to determine the region in which the epitope recognized by monoclonal antibodies 12G6, 7G6 and 11B10 was present, and the key epitope amino acids recognized.

1. Materials and Methods:

(1) Parent virus: influenza B viruses, B/Singapore/3/1964 and B/Xiamen/1346/2008 (Victoria lineage), were selected as parent viruses for escape mutation screening.

(2) Monoclonal antibody: purified 12G6, 7G6 and 11B10

(3) Escape-screening method: $10^5$ $TCID_{50}$ parent virus was homogeneously mixed with a single monoclonal antibody, wherein the final concentration of the monoclonal antibody was 1 mg/ml, and the total volume was 1 ml. The virus-monoclonal antibody complex was incubated at room temperature for 4 h, and then was used for infecting MDCK cells pre-coated on a 96-well plate. After incubating the cells with the virus-monoclonal antibody complex for 2 h, the complex was removed, a maintenance medium containing 50 ug/ml monoclonal antibody was added, and the cells were further cultured at 37° C. for 48 h. The culture supernatant was subjected to hemagglutination assay. The viruses in the wells determined to be positive were escape viruses. After three cycles of plaque cloning, stable escape virus strains were obtained.

(4) Localization of escape mutation sites in the escape virus strains: the obtained escape virus strain was subjected to RT-PCR to obtain the structural gene of the virus, and the structural gene thus obtained was sequenced and was aligned with the structural gene of the parent virus so as to identify the escape mutations and the mutation sites.

(5) Localization of key epitope amino acids in 3D structure of HA: the 3D structure file of A/Florida/4/2006 (Yamagata) virus HA protein (PDB No.: 4FQJ) was downloaded from PDB database. The 3D plotting software Pymol was used to localize the receptor binding sites of HA and the key epitope amino acid sites recognized by 12G6, 7G6, 11B10 in 3D structure of HA.

2. Results and Analysis

The escape mutation results showed that all the escape mutation sites were present in the gene encoding HA1 domain of influenza B virus HA protein.

Figure 1:
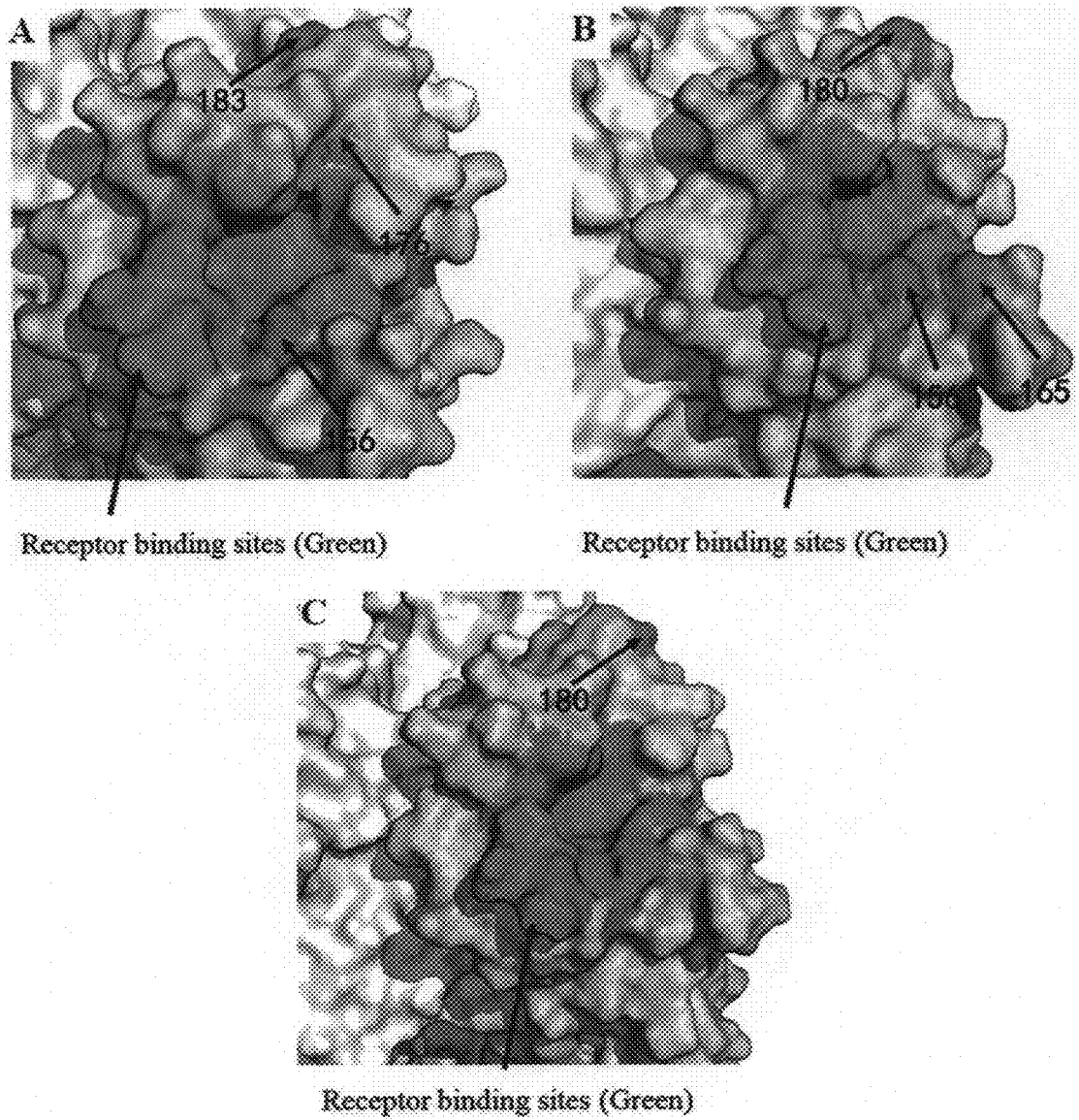
FIG. 1 shows the three-dimensional structures of the key amino acid sites in the epitopes recognized by the monoclonal antibodies 12G6 (FIG. 1A), 7G6 (FIG. 1B) and 11B10 (FIG. 1C).
Figure 2:
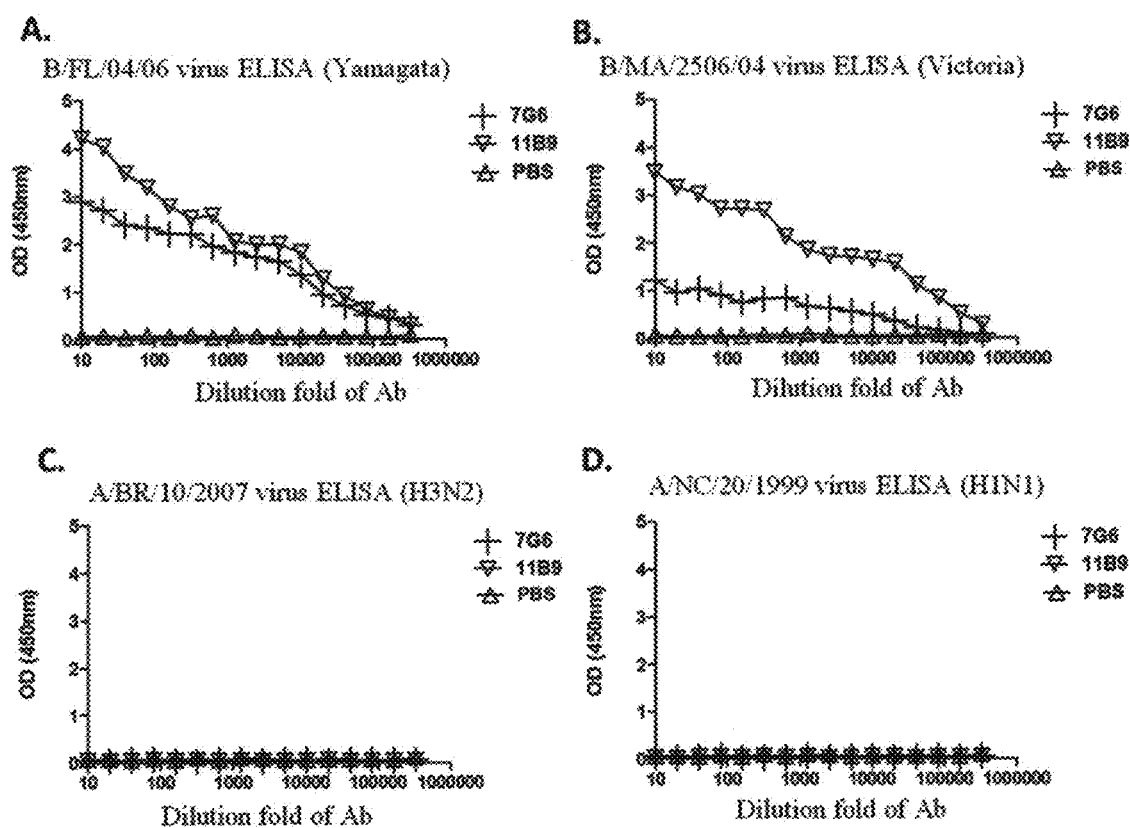
FIG. 2 shows results of ELISA assays using the monoclonal antibodies 7G6 and 11B10 to detect viruses B/Florida/04/2006 (Yamagata) (FIG. 2A), B/Malaysia/2506/2004 (Victoria) (FIG. 2B), A/Brisbane/20/2007 (H3N2) (FIG. 2C) and A/NewCalidonia/20/1999 (H1N1) (FIG. 2D), wherein the horizontal ordinate represents the dilution fold of the monoclonal antibody, and the longitudinal coordinate represents the ELISA result ($OD_{450}$). The results show that both of the monoclonal antibodies 7G6 and 11B10 have a strong binding reactivity with the two lineages of influenza B viruses, B/Florida/04/2006 (Yamagata) and B/Malaysia/2506/2004 (Victoria), but have no specific reactivity with influenza A viruses, A/Brisbane/20/2007 (H3N2) and A/NewCalidonia/20/1999 (H1N1).

In particular, the escape mutation results for the monoclonal antibody 12G6 (Table 4) showed that the escape mutation sites involved the amino acid residues at positions 156, 176 and 183 (numbering from the signal peptide, the same below) of HA protein (SEQ ID NO: 39) of B/Xiamen/1346/2008 (Victoria lineage). 15 escape virus strains were obtained by B/Xiamen/1346/2008 (Victoria lineage)-based virus escape screening, among which 4 virus strains had mutation at position 156 of HA (G156W), 4 virus strains had mutation at position 176 of HA (P176Q), and 7 virus strains had mutation at position 183 of HA (T183K). Said three amino acid sites were identified as key epitope amino acids recognized by monoclonal antibody 12G6, and the localization thereof in the 3D structure of HA was shown in FIG. 1A.

TABLE 4

The amino acid mutation sites of HA from the monoclonal antibody 12G6-induced escape strain

| Parent virus | escape mutation site in HA |
| --- | --- |
| B/Xiamen/1346/2008 | G156W (4/15)<br>P176Q (4/15)<br>T183K (7/15) |

The escape mutation results for the monoclonal antibody 7G6 (Table 5) showed that the escape mutation sites involved the amino acid residues at positions 156, 165 and 180 of HA protein (SEQ ID NO: 40) of B/Singapore/3/1964. 16 escape virus strains were obtained by B/Singapore/3/1964-based virus escape screening, among which 6 virus strains had mutation at position 156 of HA (G156W), 4 virus strains had mutation at position 165 of HA (K165E), and 6 virus strains had mutation at position 180 of HA (N180T). Said three amino acid sites were identified as key epitope amino acids recognized by monoclonal antibody 7G6, and the localization thereof in the 3D structure of HA was shown in FIG. 1B.

TABLE 5

The amino acid mutation sites of HA from the monoclonal antibody 7G6-induced escape strain

| Parent virus | escape mutation site in HA |
| --- | --- |
| B/Singapore/3/1964 | G156W (6/16)<br>K165E (4/16)<br>N180T (6/16) |

The escape mutation results for the monoclonal antibody 11B10 (Table 6) showed that the escape mutation sites involved the amino acid residue at position 180 of HA protein (SEQ ID NO: 39) of B/Xiamen/1346/2008 (Victoria lineage). 4 escape virus strains were obtained by B/Xiamen/1346/2008 (Victoria lineage)-based virus escape screening, and all had mutation at position 180 of HA (N180K). This showed that the amino acid at position 180 of HA protein was the key epitope amino acid recognized by monoclonal antibody 11B10, and the localization thereof in the 3D structure of HA was shown in FIG. 1C.

TABLE 6

The amino acid mutation sites of HA from the monoclonal antibody 11B10-induced escape strain

| Parent virus | escape mutation site in HA |
| --- | --- |
| B/Xiamen/1346/2008 | N180K (4/4) |

The experimental results showed that the monoclonal antibodies 12G6, 7G6 and 11B10 recognized similar epitopes, and the epitopes they recognized were all present in HA1 domain of influenza virus HA protein, and were close to receptor binding site (RBS) in the spatial structure.

Example 5. Separation and Sequence Analysis of Light Chain Gene and Heavy Chain Gene of Monoclonal Antibodies 12G6, 7G6 and 11B10

About $10^7$ hybridoma cells were cultured by means of semi-adherence. The adhered cells were suspended by blowing, and transferred to a new 4 ml centrifuge tube. After centrifugation at 1500 rpm for 3 min, the cell precipitate was collected and re-suspended in 100 µl sterile PBS (pH=7.45), and then transferred to a new 1.5 ml centrifuge tube. 800 µl Trizol (Roche, Germany) was added, mixed gently by reverse mixing, and then standing for 10 min. 200 µl chloroform was added, shaken vigorously for 15 s, standing for 10 min, and then centrifuged at 4° C., 12000 rpm for 15 min. The supernatant liquid was transferred to a new 1.5 ml centrifuge tube, and an equal volume of isopropanol was added, mixed, standing for 10 min, and then centrifuged at 4° C., 12000 rpm for 10 min. The supernatant was removed, 600 µl of 75% ethanol was added for washing, and then centrifuged at 4° C., 12000 rpm for 5 min. The supernatant was removed, and the precipitate was dried under vacuum at 60° C. for 5 min. The transparent precipitate was dissolved in 70 ul DEPC H₂O, and was collected into two tubes. To each tube, 1 µl reverse transcription primer was added, wherein the reverse transcription primer added to one tube was MVJkR (5'-CCGTTTGKATYTCCAGCT TGGTSCC-3') (SEQ ID NO: 31), for amplification of the gene encoding the light chain variable region, and the reverse transcription primer added to the other tube was MVDJhR (5'-CGGT-GACCGWGGTBCCTTGRCCCCA-3') (SEQ ID NO: 32), for amplification of the gene encoding the heavy chain variable region. To each tube, 1 μl dNTP (Sangon Biotech (Shanghai) Co., Ltd.) was added, and the tubes were placed in 72° C. water bath for 10 min and then immediately in an ice bath for 5 min. 10 μl 5× reverse transcription buffer, 1 μl AMV (10 u/ul, Promega), and 1 μl Rnasin (40 u/μl, Promega) were added. After mixing the mixture well, RNA was reverse-transcripted into cDNA at 42° C.

The gene of the variable region of the antibody was separated by polymerase chain reaction (PCR) method. The primer set (as shown in Table 7) and another two designed and synthesized downstream primers MVJkR (SEQ ID NO:31) and MVDJhR (SEQ ID NO:32) (synthesized by ShangHai Boya Company) were used, wherein MVJkR was a downstream primer for amplification of the gene encoding the light variable region, and MVDJhR was a downstream primer for amplification of the gene encoding the heavy variable region. The templates were the two cDNA as synthesized in the previous step. PCR conditions were: 94° C. 5 min; (94° C. 40 s, 53° C. 1 min, 72° C. 50 s)×35 cycles; 72° C. 15 min. The fragments of interest were recovered and were cloned to pMD 18-T vector, and then were sent to ShangHai Boya Company for sequencing. By blast alignment, the gene sequences encoding the antibody variable regions were determined, and the corresponding amino acid sequences were determined.

By the above method, the genes encoding the antibody variable regions were cloned from the hybridoma cell lines 12G6, 7G6, 11B10, and the amino acid sequences of complementary determinant regions (CDRs) of the monoclonal antibodies were determined by reference to Kabat method (Kabat E A, Wu T T, Perry H M, Gottesman K S, Coeller K. Sequences of proteins of immunological interest, U.S Department of Health and Human Services, PHS, NIH, Bethesda, 1991). The results were shown in Tables 8a-8b.

TABLE 7

Sequences of upstream primers for amplification of variable region genes of monoclonal antibodies 12G6, 7G6, 11B10

| Variable region gene | Name of upstream primer | Sequence of upstream primer |
|---|---|---|
| 12G6Vh | MuIgVh5'-B2 (SEQ ID NO: 33) | 5'-ATGGACTCCAGGCTCAATTTAGTTTTCCT-3' |
| 12G6Vk | MuIgkVI5'-F4 (SEQ ID NO: 34) | 5'-ATGAAGTTGCCTGTTAGGCTGTTGGTGCT-3' |
| 7G6Vh | MuIgVh5'-B2 (SEQ ID NO: 35) | 5'-ATGGACTCCAGGCTCAATTTAGTTTTCCT-3' |
| 7G6Vk | MuIgkV15'-B (SEQ ID NO: 36) | 5'-ATGGAGACAGACACACTCCTGCTAT-3' |
| 11B10Vh | MuIgVh5'-B1 (SEQ ID NO: 37) | 5'-ATGRAATGSASCTGGGTYWTYCTCTT-3' |
| 11B10Vk | MuIgkVI5'-G2 (SEQ ID NO: 38) | 5'-ATGGTYCTYATVTCCTTGCTGTTCTGG-3' |

TABLE 8a

Amino acid sequences of CDRs of monoclonal antibodies 12G6, 7G6, 11B10

| CDR | | Monoclonal antibody | | |
|---|---|---|---|---|
| | No. | 12G6 | 7G6 | 11B10 |
| heavy chain | CDR1 | GYTFTDYY (SEQ ID NO: 1) | GYTFTDYN (SEQ ID NO: 7) | GYTFTGYN (SEQ ID NO: 13) |
| | CDR2 | VNPYSGGT (SEQ ID NO: 2) | IYPNNGGT (SEQ ID NO: 8) | IYPNNGVT (SEQ ID NO: 14) |
| | CDR3 | ARWDYGVYEGYIDY (SEQ ID NO: 3) | VRSGAYYFNYLVPYFDY (SEQ ID NO: 9) | VRSGAYYVNYLVPYFDY (SEQ ID NO: 15) |
| light chain | CDR1 | EKIYSN (SEQ ID NO: 4) | ESVDIYGNSF (SEQ ID NO: 10) | ESIDIYGNSF (SEQ ID NO: 16) |
| | CDR2 | AAI (SEQ ID NO: 5) | LAS (SEQ ID NO: 11) | RAS (SEQ ID NO: 17) |
| | CDR3 | QHFWGTPLT (SEQ ID NO: 6) | QQNYEDPWT (SEQ ID NO: 12) | QQNYEDPWT (SEQ ID NO: 18) |

TABLE 8b

Amino acid sequences and nucleotide sequences of variable regions of monoclonal antibodies 12G6, 7G6, 11B10

| | |
|---|---|
| amino acid sequence of VH of 12G6 (SEQ ID NO: 19) | EVHLQQSGPELVKPGASVKMSCEASGYTFTDYYVAWVKQSPGESFEWIG RVNPYSGGTSYNQKFKGKATLIVDKSSSTAYMELSSLTSEDSAVYYCAR WDYGVYEGYIDYWGQGSALTV |
| amino acid sequence of VL of 12G6 (SEQ ID NO: 20) | DIQMTQSPASLSVSVGETVTITCRASEMYSNLAWYQQKEGKSPQLLVYA AIRLADGVPSRFSGSGSGTQFSLKINSLQSEDFGTYYCQHFWGTPLTFGAG TKLELK |
| amino acid sequence of VH of 7G6 (SEQ ID NO: 21) | EVQLQQSGPELVKPGASVKISCKASGYTFTDYNMHWVKQSLGKSLEWIG YIYPNNGGTGYNQKFESKATLTVDNSSSTAYMELRTLTSEDSAVYYCVRS GAYYFNYLVPYFDYWGQGTTLTVSS |
| amino acid sequence of VL of 7G6 (SEQ ID NO: 22) | NIVLTQSPASLAVSLGQRATISCRASESVDIYGNSFMHWYQQKPGQPPKL LIYLASKLECGVCARFNGSGCRTDFTLAFDPVEGDDGATYYCQQNYEDP WTFGGGTKLEIK |
| amino acid sequence of VH of 11B10 (SEQ ID NO: 23) | EVQLQQSGPELVKPGASVKISCKASGYTFTGYNMHWVKQSHGKSLEWIG KIYPNNGVTGYNQEFRSKATLTVDNSSSTAYMELRSLTSEDSAIYFCVRS GAYYVNYLVPYFDYWGQGTTLTVSS |
| amino acid sequence of VL of 11B10 (SEQ ID NO: 24) | NIVLIQSPASLAVSPGQRATISCRASESIDIYGNSFMHWYQKKPGQPPKLLI YRASNLESGVPARFNGSGSRTDFILTIDPVEGDDGATYYCQQNYEDPWT FGGGTKLEIK |
| nucleotide sequence of VH gene of 12G6 (SEQ ID NO: 25) | GAGGTCCACCTGCAACAGTCTGGACCTGAGCTGGTGAAGCCTGGGGC TTCAGTGAAGATGTCCTGCAAGGCTTCTGGATACACATTCACTGACTA CTACGTGGCCTGGGTGAAGCAGAGCCCTGGAGAAAGCTTTGAGTGGA TTGGACGTGTTAATCCTTACAGTGGTGGTACTAGTTACAACCAGAAGT TCAAGGGCAAGGCCACATTGATTGTTGACAAGTCCTCCAGCACAGCCT ACATGGAGCTCAGCAGCCTGACATCTGAGGACTCTGCGGTCTATTACT GTGCTAGATGGGACTATGGTGTCTACGAGGGGTACATTGACTACTGGG GCCAAGGCTCCGCTCTCACAGTCTC |
| nucleotide sequence of VL of 12G6 (SEQ ID NO: 26) | GACATCCAGATGACTCAGTCTCCAGCCTCCCTATCTGTATCTGTGGGA GAAACTGTCACCATCACATGTCGAGCAAGTGAGAAAATTTACAGTAA TTTAGCATGGTATCAGCAGAAAGAGGGAAAATCTCCTCAGCTCCTGGT CTATGCTGCAATAAGATTAGCAGATGGTGTGCCATCAAGGTTCAGTGG CAGTGGATCAGGCACACAGTTTTCCCTCAAGATCAACAGCCTGCAGTC TGAAGATTTGGGACTTATTACTGTCAACATTTTTGGGGTACTCCICTC ACGTTCGGTGCTGGGACCAAGCTGGAGCTGAAAC |
| nucleotide sequence of VH gene of 7G6 (SEQ ID NO: 27) | GAGGTCCAGCTTCAGCAGTCAGGACCTGAGCTGGTGAAACCTGGGGC CTCAGTGAAGATATCCTGCAAGGCTTCTGGATACACATTCACTGACTA CAACATGCACTGGGTGAAGCAGAGCCTTGGAAAGAGCCTTGAGTGGA TTGGATATATTTATCCTAACAATGGTGGTACTGGCTACAATCAGAAGT TCGAGAGTAAGGCCACATTGACTGTAGACAATTCCTCCAGCACAGCCT ACATGGAGCTCCGCACCCTGACATCTGAGGACTCTGCAGTCTATTACT GTGTAAGATCAGGAGCCTACTATTTTAACTACCTAGTCCCCTACTTTG ACTACTGGGGCCAAGGCACCACTCTCACAGTCTCCTCA |
| nucleotide sequence of VL gene of 7G6 (SEQ ID NO: 28) | AACATTGTGCTGACCCAATCTCCAGCTTCTTTGGCTGTGTCTCTAGGGC AGAGGGCCACCATATCTTGCAGAGCCAGTGAAAGTGTTGATATTTATG GCAATAGTTTTATGCACTGGTACCAGCAGAAACCAGGACAGCCACCC AAACTCCTCATTTATCTTGCATCCAAACTAGAATGTGGGGTGTGTGCC AGGTTCAATGGCAGTGGGTGTAGGACAGACTTCACCCTCGCTATTGAT CCTGTGGAGGGTGATGATGGTGCAACCTATTACTGTCAGCAAAATTAT GAGGATCCGTGGACGTTCGGTGGAGGCACCAAGCTGGAAATCAAAC |
| nucleotide sequence of VH gene of 11B10 (SEQ ID NO: 29) | GAGGTCCAGCTTCAGCAGTCAGGACCTGAGCTGGTGAAACCTGGGGC CTCAGTGAAGATATCCTGCAAGGCTTCTGGATACACATTCACTGGCTA CAACATGCACTGGGTGAAGCAGAGCCATGGAAAGAGCCTTGAGTGGA TTGGAAAAATTTATCCTAACAATGGTGTTACTGGCTACAACCAGGAGT TCAGGAGCAAGGCCACATTGACTGTAGACAATTCCTCCAGCACAGCCT ACATGGAGCTCCGCAGCCTGACATCTGAGGACTCTGCAATCTATTTCT GTGTAAGATCAGGAGCCTACTATGTTAACTACCTAGTCCCCTACTTTG ACTACTGGGGCCAAGGCACCACTCTCACAGTTTCCTCA |
| nucleotide sequence of VL gene of 11B10 (SEQ ID NO: 30) | AACATTGTGCTGACCCAATCTCCAGCTCTTTGGCTGTGTCTCCAGGG CAGAGGGCCACCATATCCTGCAGAGCCAGTGAAAGTATTGATATTTAT GGCAATAGTTTTATGCACTGGTACCAGAAGAAACCAGGACAGCCACC CAAACTCCTCATTTATCGTGCATCCAACCTAGAATCTGGGGTCCCTGC CAGGTTCAATGGCAGTGGGTCTAGGACAGACTTCACCCTCACCATTGA TCCTGTGGAGGGTGATGATGGTGCAACCTATTACTGTCAACAAAATTA TGAGGATCCGTGGACGTTCGGTGGAGGTACCAAGCTGGAAATCAAAC |

Example 6. Application of Monoclonal Antibodies 7G6 and 11B10 for Detection of Influenza B Virus 1. Materials and Methods (1) Preparation of influenza virus: a given amount of the following influenza virus strains: B/Florida/04/2006 (Yamagata), B/Malaysia/2506/2004(Victoria), A/Brisbane/20/2007 (H3N2), A/NewCalidonia/20/1999(H1N1), were inactivated with 0.03% formalin at 4° C. The inactivated virus was subjected to sucrose density gradient centrifugation in a super-centrifuge, and centrifuged at 4° C., 25200 rpm for 3 h. The virus precipitate was dissolved in 1×PBS at 4° C. overnight. The super-centrifuged virus was determined by HA titration, to determine the titer of the virus solution.

(2) Monoclonal antibody: the monoclonal antibodies 7G6 and 11B10 as prepared above; the concentration of the monoclonal antibody was 1 mg/ml.

(3) ELISA Experiment:

The titer of the super-centrifuged virus was adjusted to 128HA, and pre-coated onto a 96-well polystyrene ELISA plate, at 200 ul per well. The 96-well plate was then blocked with a blocking liquid. The monoclonal antibody to be tested was diluted to 0.1 mg/ml as the initial concentration, and then subjected to two-fold gradient dilution for 15 times. The diluted monoclonal antibody was added to the ELISA plate, at a volume of 100 ul per well, and incubated at 37° C. for 30 min. The ELISA plate was washed with ELISA washing solution (PBST) for 5 times, and 100 ul diluted HRP-labeled secondary antibody was then added, and the resultant mixture was incubated at 37° C. for 30 min. After washing the ELISA plate with PBST for 5 times, a chromogenic agent was added, and the color was developed for 20 min. The absorption value A450 was then read on an ELISA Reader.

2. Results and Analysis

ELISA results were shown in FIG. 2. As shown in FIG. 2, monoclonal antibodies 7G6 and 11B10 had a strong binding reactivity with two HA lineages (i.e., Yamagata and Victoria) of influenza B viruses (B/Florida/04/2006 (Yamagata) and B/Malaysia/2506/2004(Victoria)), but had no specific reactivity with the representative strains of influenza A virus (e.g., A/Brisbane/20/2007(H3N2) and A/NewCalidonia/20/1999(H1N1)).

The results showed that the broad-spectrum monoclonal antibodies 7G6 and 11B10 can be used to specifically detect at least two HA lineages of influenza B viruses.

Example 7. Application of Monoclonal Antibodies 12G6, 7G6 and 11B10 for Treatment of Influenza Virus Infection Passive immunotherapy of infectious diseases with antibodies is a potentially effective route for anti-viral treatment. It was demonstrated by in vitro neutralization assay in microwells in the previous Examples that the monoclonal antibodies according to the invention had high neutralizing activity against at least two HA lineages (e.g., Yamagata and Victoria) of influenza B viruses isolated from different regions at different times. The monoclonal antibodies according to the invention were characterized by a broad neutralizing reactivity spectrum against at least two HA lineages (e.g., Yamagata and Victoria) of influenza B viruses, and a high neutralizing titer. To further demonstrate the anti-viral effect of the monoclonal antibodies according to the invention in vivo, the monoclonal antibodies according to the invention was verified for the anti-viral therapeutic effect on the infection by Yamagata lineage and Victoria lineage of influenza B virus in an Animal Biosafety laboratory, based on Yamagata lineage and Victoria lineage of influenza B virus-infected Balb/C mice. The experiment was as followed.

(1) Materials and Methods

Animal: Balb/C mice, SPF, 6-8-week-old, female, weighed about 20 g.

Monoclonal antibody: 12G6, 7G6, 11B10

Mouse adaptive strain of influenza B virus:

a mouse adaptive strain of Yamagata lineage of influenza B virus: B/Florida/04/2006, called FL04-MA for short;

a mouse adaptive strain of Victoria lineage of influenza B virus: B/Brisbane/60/2008, called BR60-MA for short.

Anesthetic: Isoflorane

Animal grouping: mice were sent to the Animal Biosafety laboratory one day ahead, and were divided into groups, with 5 mice per cage, designated as G1, G2, etc.; the weight of each mouse was recorded, the regimens were shown in Table 9.

Virus infection: Yamagata lineage virus B/Florida/04/2006 was pre-diluted to $10^5$ $TCID_{50}$/ul, Victoria lineage virus B/Brisbane/60/2008 was pre-diluted to $10^6$ $TCID_{50}$/ul, and the mice were inoculated with the virus at a dose of 50 μl/mouse. Before inoculation, mice were anesthetized with isoflorane, and then infected by inoculation of virus via nasal cavity.

MAb intervention: 24 h (dpi.1) after virus infection, the mice in antibody-treatment group were injected with antibody at a given dose, i.e. 10 mg/kg, wherein the injection volume was MOW/mouse.

Observation: 1-14 days after virus infection, weight, survival, and the corresponding behavioral symptoms of mice were recorded every day.

TABLE 9

| Experimental regimen | | | | |
|---|---|---|---|---|
| Group | Note | Infectious virus | MAb intervention | Number of mice |
| 12G6 experimental regimen | | | | |
| G1 | Blank control group | PBS | PBS | 5 |
| G2 | Y lineage therapeutic group | FL04-MA | 12G6 10 mg/kg | 5 |
| G3 | Y lineage virus control group | FL04-MA | — | 5 |
| G4 | Blank control group | PBS | PBS | 5 |
| G5 | V lineage therapeutic group | BR60-MA | 12G6 10 mg/kg | 5 |
| G6 | V lineage virus control group | BR60-MA | — | 5 |

TABLE 9-continued Experimental regimen

| Group | Note | Infectious virus | MAb intervention | Number of mice |
|---|---|---|---|---|
| 7G6 experimental regimen | | | | |
| G7 | Blank control group | PBS | PBS | 5 |
| G8 | Y lineage therapeutic group | FL04-MA | 7G6 10 mg/kg | 5 |
| G9 | Y lineage virus control group | FL04-MA | — | 5 |
| G10 | Blank control group | PBS | PBS | 5 |
| G11 | V lineage therapeutic group | BR60-MA | 7G6 10 mg/kg | 5 |
| G12 | V lineage virus control group | BR60-MA | — | 5 |
| 11B10 experimental regimen | | | | |
| G13 | Blank control group | PBS | PBS | 5 |
| G14 | Y lineage therapeutic group | FL04-MA | 11B10 10 mg/kg | 5 |
| G15 | Y lineage virus control group | FL04-MA | — | 5 |
| G16 | Blank control group | PBS | PBS | 5 |
| G17 | V lineage therapeutic group | BR60-MA | 11B10 10 mg/kg | 5 |
| G18 | V lineage virus control group | BR60-MA | — | 5 |

(2) Results and Analysis

Mice were separately infected by Yamagata lineage of influenza B virus FL04-MA and Victoria lineage of influenza B virus BR60-MA at a one-week lethal dose. 1 day after infection, the antibody was injected to the caudal vein of mice in the therapeutic group. The therapeutic effect of the monoclonal antibody was determined by measuring the body weight and calculating the survival rate of mice in each group. The experimental results were shown in FIGS. 3-5.

The experimental results in FIG. 3-5 showed that no significant weight fluctuation was observed in mice in the negative control group during the whole experiment; significant weight loss was observed in two virus-infected control groups. All the mice in FL04-MA virus control group died 8 days after infection; and all the mice in BR60-MA virus control group died 5-10 days after infection. In the case of said two influenza B viruses, 12G6, 7G6, 11B10 antibody-injection intervention at a dose of 10 mg/kg could lead to weight recovery in the infected mice (FIGS. 3B, 3D, 4B, 4D, 5B, and 5D). In addition, the survival of mice was observed 1-14 days after virus infection. The results showed that monoclonal antibody 12G6, 7G6, 11B10 at a dose of 10 mg/kg could enable the mice infected by virus survive normally for 14 days, and the treatment effectiveness reached 100% (FIGS. 3A, 3C, 4A, 4C, 5A, and 5C). The results showed that the broad-spectrum monoclonal antibodies according to the invention can effectively prevent and treat the infection by the two HA lineages of influenza B viruses and the diseases caused thereby.

Example 8. Function of Monoclonal Antibody 12G6

1. Monoclonal Antibody 12G6 can Inhibit the Entry of Influenza B Virus into a Host Cell.

(1) Materials and Methods

Virus: B/Florida/4/2006(Yamagata), and B/Brisbane/60/2008 (Victoria);

HA-specific antibody: monoclonal antibody 12G6, polyclonal antiserum against B/Florida/4/2006 virus, and polyclonal antiserum against B/Malaysia/2506/2004 virus;

rabbit polyclonal antiserum specifically against influenza B virus NP protein;

GAM-FITC (FITC-labeled goat anti-mouse antibody, green fluorescence);

Cell: MDCK cell;

The monoclonal antibody 12G6 (10 μg/ml), polyclonal antiserum against B/Florida/4/2006 virus, polyclonal antiserum against B/Malaysia/2506/2004 virus, and PBS (an antibody-free control) were separately incubated with two lineages of influenza B viruses at 37° C. for 1 h. The incubated mixture was then added to the monolayer MDCK cells cultured in a 96-well plate, and the cells were further cultured for 16-18 h. After the culture, the cells were washed with the culture medium for three times. The cells were then subjected to DAPI staining (blue fluorescence) with a commercialized kit; and the cells were subjected to immunofluorescence analysis using rabbit polyclonal antiserum against influenza B virus NP protein (as a first antibody) and GAM-FITC (as a second antibody, green fluorescence).

(2) Results and Analysis

The experimental results were shown in FIG. 6. The results showed that when PBS was used for incubation, both of the two lineages of influenza B viruses tested could enter MDCK cells (cells showed green fluorescence). When polyclonal antiserum against B/Florida/4/2006 virus was used for incubation, B/Florida/4/2006 (Yamagata) could not enter MDCK cells (cells showed blue fluorescence), while B/Brisbane/60/2008 (Victoria) could enter MDCK cells (cells showed green fluorescence). When polyclonal antiserum against B/Malaysia/2506/2004 virus was used for incubation, B/Brisbane/60/2008(Victoria) could not enter MDCK cells (cells showed blue fluorescence), while B/Florida/4/2006(Yamagata) could enter MDCK cells (cells showed green fluorescence). When monoclonal antibody 12G6 was used for incubation, neither of the two lineages of influenza B viruses could enter MDCK cells (cells showed blue fluorescence). The results showed that monoclonal antibody 12G6 could inhibit the entry of the two lineages of influenza B viruses into a host cell.

2. Monoclonal Antibody 12G6 can Inhibit the Membrane Fusion of Influenza B Virus to a Cell.

(1) Materials and Methods

Virus: B/Florida/4/2006 (Yamagata), and B/Brisbane/60/2008 (Victoria);

HA-specific antibody: monoclonal antibody 12G6

Experimental reagents: Giemsa Stain, 10 mM MES (Sigma, Catalog number: M3671-250G) and 10 mM HEPES (Sigma, Catalog number: H3375, pH 5.5), and TPCK trypsin (Sigma, Catalog number: T1426);

Cell: MDCK cells;

At multiplicity of infection MOI=0.3, MDCK cells were infected by B/Florida/4/2006 (Yamagata) and B/Brisbane/60/2008(Victoria), respectively. 24 hours later, the cells were washed with the culture medium for three times, to remove the residuary virus. 2.5 mg/ml TPCK trypsin was then added to the cells. After incubation at 37° C. for 15 min, the cells were washed with the culture medium for three times, to remove the residuary trypsin. Later, a given concentration of antibody 12G6 (0 μg/ml, 5 μg/ml, 20 μg/ml or 100 μg/ml) was added to the cells, and incubated at 37° C. for 30 min. The antibody solution was then removed, and the cells were incubated in 10 mM MES and 10 mM HEPES (pH 5.5) at 37° C. for 2 min (allosterism easily occurs for HA protein under acidic conditions, thereby promoting the fusion of a viral envelope to a cell membrane). After washing with the culture medium for three times (after washing, the virus/cell culture environment turned from acidic to neutral), and the cells infected by virus were further cultured at 37° C. for 3 h. Later, the cells were fixed, and stained with Giemsa Stain, and membrane fusion occurred or not in the cells was observed. If an antibody can inhibit the fusion of a viral envelop to a cell membrane, no syncytium resulted from membrane fusion can be observed after staining. On the contrary, if an antibody cannot inhibit the fusion of a viral envelop to a cell membrane, syncytium resulted from membrane fusion can be observed after staining.

(2) Results and Analysis

The experimental results were shown in FIG. 7. The results showed that when no antibody 12G6 was used for incubating cells (i.e., 0 μg/ml antibody), both of the two lineages of influenza B viruses tested could result in membrane fusion of the MDCK cells (i.e., a lot of syncytia appeared). When 5 μg/ml or 20 μg/ml antibody 12G6 was used for incubation, the membrane fusion of MDCK cells was significantly inhibited (i.e., the number of syncytia decreased significantly), and 20 μg/ml antibody had a stronger inhibition than 5 μg/ml antibody. Moreover, when 100 μg/ml antibody 12G6 was used for incubation, membrane fusion of MDCK cells were completely inhibited (i.e., no syncytia appeared). The results showed that monoclonal antibody 12G6 could inhibit the membrane fusion of the two lineages of influenza B viruses to a cell; and the inhibitory activity of monoclonal antibody 12G6 was dose-dependent.

3. Monoclonal Antibody 12G6 can Inhibit the Release of Influenza B Virus from a Host Cell.

(1) Materials and Methods

Virus: B/Florida/4/2006 (Yamagata), and B/Brisbane/60/2008 (Victoria)

HA-specific antibody: monoclonal antibody 12G6, and negative control antibody (anti-HIV mAb 5G6);

rabbit polyclonal antiserum specifically against NP protein of influenza B virus;

GAM-HRP;

Cell: MDCK cells;

MDCK cells were inoculated onto a 96-well plate at a density of 40000 cells/well. 4 hours later, and an excessive amount of influenza B virus was added to the cells, to infect the cells. 3 h after the infection, the virus solution was removed, and the cells were washed with PBS for 3 times, to remove the free viruses. To the cell culture plate, a culture medium (a control free of antibody), or a given concentration of monoclonal antibody 12G6 (2 μg/ml, 0.2 μg/ml or 0.02 m/ml; diluted in the culture medium), or a given concentration of negative control antibody (20 μg/ml or 2 μg/ml; diluted in the culture medium), was added. After further incubation at 37° C. for 16-18 h, the cell supernatant and cell lysate were collected, respectively, and immunoblotting assay was carried out by using rabbit polyclonal antiserum (as a first antibody) against NP protein of influenza B virus and GAM-HRP (as a second antibody).

(2) Results and Analysis

The experimental results were shown in FIG. 8. The results showed that when no antibody or a negative control antibody was used for incubating the MDCK cells infected by influenza B virus, a significant amount of NP protein could be detected in the cultured supernatant and cell lysate. This showed that the two lineages of influenza B viruses could be proliferated in MDCK cells, and had been released from the cells; and the negative control antibody could not inhibit the release of influenza B virus from the host cells. In contrast, when monoclonal antibody 12G6 was used for incubating the MDCK cells infected by influenza B virus, NP protein could be detected in the cell lysate, but the amount of NP protein in the cultured supernatant decreased with the increase of the concentration of the monoclonal antibody 12G6. When the concentration of monoclonal antibody 12G6 reached 2 m/ml, no NY protein was detected in the cultured supernatant, indicating that the release of influenza B virus was completely inhibited. These results showed that monoclonal antibody 12G6 could inhibit the release of the lineages of influenza B viruses from the host cells, and the inhibitory activity of monoclonal antibody 12G6 was dose-dependent.

4. Monoclonal Antibody 12G6 has ADCC and CDC Activity.

By the method as described by Srivastava V. et al., J Virol, 2013 May, 87(10):5831-40, ADCC and CDC activity of monoclonal antibody 12G6 were determined.

(1) Materials and Methods

Virus: B/Massachusetts/02/2012-like (Yamagata lineage), and B/Brisbane/60/2008 (Victoria lineage);

HA-specific antibody: 12G6, and negative control antibody (anti-HIV mAb 5G6);

Cell: MDCK cells, and mouse NK cells;

Cell staining reagent: PKH-67(SIGMA-ALDRICH, Catalog number: PKH67GL; as conventional cell membrane dye), and 7-AAD (eBioscience, Catalog number: 00-6993-50; as nucleic acid dye, for identifying dead cells);

Mouse NK Cell Isolation Kit (NK Cell Isolation Kit II mouse, manufacturer: MACS, Catalog number: 130-096-892) was used to isolate NK cells from mouse spleen (i.e., effector cell), for further use. At multiplicity of infection MOI=10, MDCK cells (i.e., target cells) were infected by influenza B virus. 3 h later, at a cell concentration of $1\times10^5$ cells/mL, 100 μl cells were seeded in a 96-well plate. After culturing for 1 h, the membrane of the MDCK cells was stained with PKH-67 dye. After staining, the antibody to be tested was diluted to a given concentration (20 μg/ml, 2 μg/ml, or 0.5 μg/ml), and added to the cells in the culture plate at a volume of 50 μl/well, and the cells were then incubated at 37° C. for 15 min. Later, for ADCC assay, the effector cells (100 μl) were added to the cells in the culture plate, at a ratio of effector cells to target cells being 50:1; for CDC assay, 100-fold diluted guinea pig serum (1000) as a complement, was added to the cells in the culture plate. The culture plate was incubated at 37° C. for 2 h, and then the dye 7-AAD was added at a volume of 1 μl/well, and the resultant mixture was incubated for 5 min. After the incubation, the cells were analyzed by flow cytometer, and the percentage of the dead target cells was calculated. In addition, the experiment was repeated under the conditions where no antibody was used, as background control, which represented the spontaneous lysis rate of the infected target cells incubated with the effector cells. In addition, 1% Triton X-100 (in place of the antibody to be tested) was used to repeat the experiment, as positive control, which represented the maximum lysis rate of the infected target cells incubated with the effector cells.

The fluorescence staining states for these cells were as followed: living effector cells, no fluorescence; dead effector cells, 7-AAD staining (far-red light); living target cells, PKH-67 staining (green light); dead target cells, PKH-67 and 7-AAD double staining (far-red light and green light). ADCC and CDC activity were calculated as followed:

> ADCC activity or CDC activity=(percentage of dead target cells in a test group−percentage of dead target cells in a background control group)/(percentage of dead target cells in a positive control group−percentage of dead target cells in a background control group)*100%

(2) Results and Analysis

The experimental results were shown in FIG. 9. The results showed that when a negative control antibody was used for incubation, no obvious lysis occurred in the virus-infected MDCK cells in the presence of NK cells or guinea pig serum. This showed that the negative control antibody could not trigger the ADCC and CDC against the tested two lineages of influenza B viruses. In contrast, when the antibody 12G6 was used for incubation, obvious lysis occurred in the virus-infected MDCK cells in the presence of NK cells or guinea pig serum; and, with the increase of the antibody concentration used, the lysis of MDCK cells was enhanced. These results showed that monoclonal antibody 12G6 could trigger the ADCC and CDC against the tested two lineages of influenza B viruses; and the activity of monoclonal antibody 12G6 was dose-dependent.

The results showed that the antibody 12G6 had multiple functional activities: capable of inhibiting the entry of a virus into a host cell, capable of inhibiting the membrane fusion of a virus to a cell, capable of inhibiting the release of a virus from a host cell, and capable of triggering antibody-dependent cell-mediated cytotoxicity (ADCC) and complement-dependent cytotoxicity (CDC) against a virus. The antibody 12G6 can neutralize influenza B virus by the five activities, and thereby prevent and treat infection by influenza B virus.

Although the specific embodiments of the invention have been described in detail, those skilled in the art would understand that, according to all the disclosed teachings, various modifications and changes can be made, and that such modifications and changes are within the scope of the present invention. The scope of the present invention is given by the appended claims and any equivalents thereof.

The invention claimed is:

1. A hybridoma cell line, selected from the group consisting of:

1) Hybridoma cell line 12G6, deposited in China Center for Type Culture Collection (CCTCC), with a deposition number of CCTCC NO: C201527;

2) Hybridoma cell line 7G6, deposited in China Center for Type Culture Collection (CCTCC), with a deposition number of CCTCC NO: C201435; and 3) Hybridoma cell line 11B10, deposited in China Center for Type Culture Collection (CCTCC), with a deposition number of CCTCC NO: C201432.

2. A monoclonal antibody or an antigen binding fragment thereof, comprising complementary determining regions (CDR) of a heavy chain variable region (VH) and complementary determining regions (CDR) of a light chain variable region (VL), wherein the monoclonal antibody or antigen binding fragment thereof comprises:

(1) VH CDR1-3 with amino acid sequences set forth in SEQ ID NO: 1-3, respectively, and VL CDR1-3 with amino acid sequences set forth in SEQ ID NO: 4-6, respectively;
(2) VH CDR1-3 with amino acid sequences set forth in SEQ ID NO: 7-9, respectively, and VL CDR1-3 with amino acid sequences set forth in SEQ ID NO: 10-12, respectively; or
(3) VH CDR1-3 with amino acid sequences set forth in SEQ ID NO: 13-15, respectively, and VL CDR1-3 with amino acid sequences set forth in SEQ ID NO: 16-18, respectively.

3. The monoclonal antibody or antigen binding fragment thereof according to claim 2, wherein the monoclonal antibody or antigen binding fragment thereof comprises:
(1) VH set forth in SEQ ID NO: 19 and VL set forth in SEQ ID NO: 20;
(2) VH set forth in SEQ ID NO: 21 and VL set forth in SEQ ID NO: 22; or
(3) VH set forth in SEQ ID NO: 23 and VL set forth in SEQ ID NO: 24.

4. The monoclonal antibody or antigen binding fragment thereof according to claim 2, wherein the monoclonal antibody or antigen binding fragment thereof has one or more of the following features:
(1) the monoclonal antibody or antigen binding fragment thereof is selected from Fab, Fab', F(ab')$_2$, Fd, Fv, dAb, complementary determining region fragment, single chain antibody, mouse antibody, humanized antibody, chimeric antibody, or bispecific or poly-specific antibody;
(2) the monoclonal antibody comprises non-CDR region, and the non-CDR region is from a species other than murine species;
(3) the monoclonal antibody is a monoclonal antibody produced by Hybridoma cell line 12G6, 7G6 or 11B10, wherein the Hybridoma cell lines 12G6, 7G6 and 11B10 have been deposited in China Center for Type Culture Collection (CCTCC), with a deposition number of CCTCC NO C201527, CCTCC NO: C201435 and CCTCC NO: C201432, respectively;
(4) the monoclonal antibody or antigen binding fragment thereof can specifically bind to HA1 domain of HA protein of Yamagata lineage and/or Victoria lineage of influenza B viruses;
(5) the monoclonal antibody or antigen binding fragment thereof has hemagglutination-inhibiting activity against Yamagata lineage of influenza B virus and/or Victoria lineage of influenza B virus;
(6) the monoclonal antibody or antigen binding fragment thereof has neutralizing activity, and can neutralize Yamagata lineage of influenza B virus and/or Victoria lineage of influenza B virus;
(7) the monoclonal antibody or antigen binding fragment thereof has an activity of inhibiting entry of Yamagata lineage and/or Victoria lineage of influenza B viruses into a host cell;
(8) the monoclonal antibody or antigen binding fragment thereof has an activity of inhibiting release of Yamagata lineage and/or Victoria lineage of influenza B viruses from a host cell;
(9) the monoclonal antibody or antigen binding fragment thereof has an activity of inhibiting membrane fusion of Yamagata lineage and/or Victoria lineage of influenza B viruses with a host cell;
(10) the monoclonal antibody or antigen binding fragment thereof has an activity of triggering ADCC against Yamagata lineage and/or Victoria lineage of influenza B viruses; and
(11) the monoclonal antibody or antigen binding fragment thereof has an activity of triggering CDC against Yamagata lineage and/or Victoria lineage of influenza B viruses.

5. A pharmaceutical composition, comprising the monoclonal antibody or antigen binding fragment thereof according to claim 2 or an anti-idiotype antibody which is specifically directed to the idiotype of said monoclonal antibody, and a pharmaceutically acceptable carrier and/or excipient.

6. A composition, comprising anyone of the following:
(1) the monoclonal antibody or antigen binding fragment thereof according to claim 2;
(2) an isolated nucleic acid molecule encoding the monoclonal antibody or antigen binding fragment thereof of (1);
(3) a vector comprising the isolated nucleic acid molecule of (2);
(4) an isolated host cell comprising the isolated nucleic acid molecule of (2); and
(5) an anti-idiotype antibody, which is specifically directed to the idiotype of the monoclonal antibody of (1).

7. A kit, comprising the monoclonal antibody or antigen binding fragment thereof according to claim 2 with or without a detectable marker; and optionally,
a second antibody, which specifically recognizes the monoclonal antibody or antigen binding fragment thereof and is optionally labeled by a detectable marker.

8. An isolated nucleic acid molecule, encoding the monoclonal antibody or antigen binding fragment thereof according to claim 2.

9. A vector, comprising the isolated nucleic acid molecule according to claim 8.

10. An isolated host cell, comprising the isolated nucleic acid molecule according to claim 8 or a vector comprising said isolated nucleic acid molecule.

11. An anti-idiotype antibody, which is specifically directed to the idiotype of the monoclonal antibody according to claim 2.

12. A method for producing a monoclonal antibody or antigen binding fragment thereof, comprising culturing the host cell according to claim 10 under suitable conditions to express the monoclonal antibody or antigen binding fragment thereof, and recovering the monoclonal antibody or antigen binding fragment thereof from the cell culture.

13. A method for detecting the presence or level of influenza B virus or HA protein thereof in a sample, comprising (1) contacting the monoclonal antibody or antigen binding fragment thereof according to claim 2 with a sample having or suspected to have influenza B virus or HA protein thereof, and (2) detecting any binding between the monoclonal antibody or antigen binding fragment thereof and HA protein of influenza B virus.

14. A method for neutralizing virulence of influenza B virus in a sample, comprising contacting a sample comprising influenza B virus with the monoclonal antibody or antigen binding fragment thereof according to claim 2.

15. A method for diagnosing whether a subject is infected by influenza B virus, comprising (1) contacting the monoclonal antibody or antigen binding fragment thereof according to claim 2 with a sample from a subject that is suspected to be infected by influenza B virus, and (2) detecting the presence of influenza B virus in the sample by detecting any binding between the monoclonal antibody or antigen binding fragment thereof and HA protein of influenza B virus.

16. A method for inhibiting or treating an infection by influenza B virus or a disease associated with the infection in a subject, comprising administering a prophylactically or therapeutically effective amount of the monoclonal antibody or antigen binding fragment thereof according to claim 2 to a subject in need thereof.

17. The method of claim 16, characterized by one or more of the following features:

(1) the subject is a human;

(2) the influenza B virus is selected from Yamagata lineage and Victoria lineage of influenza B viruses;

(3) the monoclonal antibody or antigen binding fragment thereof is administered alone, or in combination with an additional anti-influenza agent; and (4) the disease associated with the infection is influenza.

* * * * *

UNITED STATES PATENT AND TRADEMARK OFFICE
CERTIFICATE OF CORRECTION

PATENT NO. : 10,696,736 B2
APPLICATION NO. : 15/732536
DATED : June 30, 2020
INVENTOR(S) : Yixin Chen et al.

Page 1 of 1

It is certified that error appears in the above-identified patent and that said Letters Patent is hereby corrected as shown below:

On the Title Page

Item (30), the Foreign Application Priority Data is incorrect. Item (30) should read:
-- (30) Foreign Application Priority Data
Jun. 3, 2015 (CN) ............................... 201510295723.3 --

Signed and Sealed this
Eighth Day of September, 2020

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: heavy chain CDR1 of 12G6

<400> SEQUENCE: 1

Gly Tyr Thr Phe Thr Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: heavy chain CDR2 of 12G6

<400> SEQUENCE: 2

Val Asn Pro Tyr Ser Gly Gly Thr
1               5

<210> SEQ ID NO 3
<211> LENGTH: 14
<212> TYPE: PRT
<213> ORGANISM: Artificial Sequence
<220> FEATURE:
<223> OTHER INFORMATION: heavy chain CDR3 of 12G6

<400> SEQUENCE: 3

Ala Arg Trp Asp Tyr Gly Val Tyr Glu Gly Tyr Ile Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: light chain CDR1 of 12G6
```

```
<400> SEQUENCE: 4

Glu Lys Ile Tyr Ser Asn
1               5

<210> SEQ ID NO 5
<211> LENGTH: 3
<212> TYPE: PRT
<213> ORGANISM: Artificial Sequence
<220> FEATURE:
<223> OTHER INFORMATION: light chain CDR2 of 12G6

<400> SEQUENCE: 5

Ala Ala Ile
1

<210> SEQ ID NO 6
<211> LENGTH: 9
<212> TYPE: PRT
<213> ORGANISM: Artificial Sequence
<220> FEATURE:
<223> OTHER INFORMATION: light chain CDR3 of 12G6

<400> SEQUENCE: 6

Gln His Phe Trp Gly Thr Pro Leu Thr
1               5

<210> SEQ ID NO 7
<211> LENGTH: 8
<212> TYPE: PRT
<213> ORGANISM: Artificial Sequence
<220> FEATURE:
<223> OTHER INFORMATION: heavy chain CDR1 of 7G6

<400> SEQUENCE: 7

Gly Tyr Thr Phe Thr Asp Tyr Asn
1               5

<210> SEQ ID NO 8
<211> LENGTH: 8
<212> TYPE: PRT
<213> ORGANISM: Artificial Sequence
<220> FEATURE:
<223> OTHER INFORMATION: heavy chain CDR2 of 7G6

<400> SEQUENCE: 8

Ile Tyr Pro Asn Asn Gly Gly Thr
1               5

<210> SEQ ID NO 9
<211> LENGTH: 17
<212> TYPE: PRT
<213> ORGANISM: Artificial Sequence
<220> FEATURE:
<223> OTHER INFORMATION: heavy chain CDR3 of 7G6

<400> SEQUENCE: 9

Val Arg Ser Gly Ala Tyr Tyr Phe Asn Tyr Leu Val Pro Tyr Phe Asp
1               5                   10                  15

Tyr

<210> SEQ ID NO 10
<211> LENGTH: 10
<212> TYPE: PRT
<213> ORGANISM: Artificial Sequence
<220> FEATURE:
```

```
<223> OTHER INFORMATION: light chain CDR1 of 7G6

<400> SEQUENCE: 10

Glu Ser Val Asp Ile Tyr Gly Asn Ser Phe
1               5                   10

<210> SEQ ID NO 11
<211> LENGTH: 3
<212> TYPE: PRT
<213> ORGANISM: Artificial Sequence
<220> FEATURE:
<223> OTHER INFORMATION: light chain CDR2 of 7G6

<400> SEQUENCE: 11

Leu Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: light chain CDR3 of 7G6

<400> SEQUENCE: 12

Gln Gln Asn Tyr Glu Asp Pro Trp Thr
1               5

<210> SEQ ID NO 13
<211> LENGTH: 8
<212> TYPE: PRT
<213> ORGANISM: Artificial Sequence
<220> FEATURE:
<223> OTHER INFORMATION: heavy chain CDR1 of 11B10

<400> SEQUENCE: 13

Gly Tyr Thr Phe Thr Gly Tyr Asn
1               5

<210> SEQ ID NO 14
<211> LENGTH: 8
<212> TYPE: PRT
<213> ORGANISM: Artificial Sequence
<220> FEATURE:
<223> OTHER INFORMATION: heavy chain CDR2 of 11B10

<400> SEQUENCE: 14

Ile Tyr Pro Asn Asn Gly Val Thr
1               5

<210> SEQ ID NO 15
<211> LENGTH: 17
<212> TYPE: PRT
<213> ORGANISM: Artificial Sequence
<220> FEATURE:
<223> OTHER INFORMATION: heavy chain CDR3 of 11B10

<400> SEQUENCE: 15

Val Arg Ser Gly Ala Tyr Tyr Val Asn Tyr Leu Val Pro Tyr Phe Asp
1               5                   10                  15

Tyr

<210> SEQ ID NO 16
<211> LENGTH: 10
<212> TYPE: PRT
<213> ORGANISM: Artificial Sequence
```

```
<220> FEATURE:
<223> OTHER INFORMATION: light chain CDR1 of 11B10

<400> SEQUENCE: 16

Glu Ser Ile Asp Ile Tyr Gly Asn Ser Phe
1               5                   10

<210> SEQ ID NO 17
<211> LENGTH: 3
<212> TYPE: PRT
<213> ORGANISM: Artificial Sequence
<220> FEATURE:
<223> OTHER INFORMATION: light chain CDR2 of 11B10

<400> SEQUENCE: 17

Arg Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: light chain CDR3 of 11B10

<400> SEQUENCE: 18

Gln Gln Asn Tyr Glu Asp Pro Trp Thr
1               5

<210> SEQ ID NO 19
<211> LENGTH: 119
<212> TYPE: PRT
<213> ORGANISM: Artificial Sequence
<220> FEATURE:
<223> OTHER INFORMATION: heavy chain variable region of 12G6

<400> SEQUENCE: 19

Glu Val His Leu Gln Gln Ser Gly Pro Glu Leu Val Lys Pro Gly Ala
1               5                   10                  15

Ser Val Lys Met Ser Cys Glu Ala Ser Gly Tyr Thr Phe Thr Asp Tyr
            20                  25                  30

Tyr Val Ala Trp Val Lys Gln Ser Pro Gly Glu Ser Phe Glu Trp Ile
        35                  40                  45

Gly Arg Val Asn Pro Tyr Ser Gly Thr Ser Tyr Asn Gln Lys Phe
    50                  55                  60

Lys Gly Lys Ala Thr Leu Ile Val Asp Lys Ser Ser Thr Ala Tyr
65                  70                  75                  80

Met Glu Leu Ser Ser Leu Thr Ser Glu Asp Ser Ala Val Tyr Cys
                85                  90                  95

Ala Arg Trp Asp Tyr Gly Val Tyr Glu Gly Tyr Ile Asp Tyr Trp Gly
            100                 105                 110

Gln Gly Ser Ala Leu Thr Val
        115

<210> SEQ ID NO 20
<211> LENGTH: 107
<212> TYPE: PRT
<213> ORGANISM: Artificial Sequence
<220> FEATURE:
<223> OTHER INFORMATION: light chain variable region of 12G6

<400> SEQUENCE: 20

Asp Ile Gln Met Thr Gln Ser Pro Ala Ser Leu Ser Val Ser Val Gly
```

```
                1               5                  10                 15
Glu Thr Val Thr Ile Thr Cys Arg Ala Ser Glu Lys Ile Tyr Ser Asn
                               20                 25                 30

Leu Ala Trp Tyr Gln Gln Lys Glu Gly Lys Ser Pro Gln Leu Leu Val
            35                 40                 45

Tyr Ala Ala Ile Arg Leu Ala Asp Gly Val Pro Ser Arg Phe Ser Gly
        50                 55                 60

Ser Gly Ser Gly Thr Gln Phe Ser Leu Lys Ile Asn Ser Leu Gln Ser
65                 70                 75                 80

Glu Asp Phe Gly Thr Tyr Tyr Cys Gln His Phe Trp Gly Thr Pro Leu
                85                 90                 95

Thr Phe Gly Ala Gly Thr Lys Leu Glu Leu Lys
            100                105

<210> SEQ ID NO 21
<211> LENGTH: 124
<212> TYPE: PRT
<213> ORGANISM: Artificial Sequence
<220> FEATURE:
<223> OTHER INFORMATION: heavy chain variable region of 7G6

<400> SEQUENCE: 21

Glu Val Gln Leu Gln Gln Ser Gly Pro Glu Leu Val Lys Pro Gly Ala
1               5                  10                 15

Ser Val Lys Ile Ser Cys Lys Ala Ser Gly Tyr Thr Phe Thr Asp Tyr
                20                 25                 30

Asn Met His Trp Val Lys Gln Ser Leu Gly Lys Ser Leu Glu Trp Ile
            35                 40                 45

Gly Tyr Ile Tyr Pro Asn Asn Gly Gly Thr Gly Tyr Asn Gln Lys Phe
        50                 55                 60

Glu Ser Lys Ala Thr Leu Thr Val Asp Asn Ser Ser Ser Thr Ala Tyr
65                 70                 75                 80

Met Glu Leu Arg Thr Leu Thr Ser Glu Asp Ser Ala Val Tyr Tyr Cys
                85                 90                 95

Val Arg Ser Gly Ala Tyr Tyr Phe Asn Tyr Leu Val Pro Tyr Phe Asp
            100                105                110

Tyr Trp Gly Gln Gly Thr Thr Leu Thr Val Ser Ser
        115                120

<210> SEQ ID NO 22
<211> LENGTH: 111
<212> TYPE: PRT
<213> ORGANISM: Artificial Sequence
<220> FEATURE:
<223> OTHER INFORMATION: light chain variable region of 7G6

<400> SEQUENCE: 22

Asn Ile Val Leu Thr Gln Ser Pro Ala Ser Leu Ala Val Ser Leu Gly
1               5                  10                 15

Gln Arg Ala Thr Ile Ser Cys Arg Ala Ser Glu Ser Val Asp Ile Tyr
                20                 25                 30

Gly Asn Ser Phe Met His Trp Tyr Gln Gln Lys Pro Gly Gln Pro Pro
            35                 40                 45

Lys Leu Leu Ile Tyr Leu Ala Ser Lys Leu Glu Cys Gly Val Cys Ala
        50                 55                 60

Arg Phe Asn Gly Ser Gly Cys Arg Thr Asp Phe Thr Leu Ala Ile Asp
65                 70                 75                 80
```

Pro Val Glu Gly Asp Asp Gly Ala Thr Tyr Tyr Cys Gln Gln Asn Tyr
            85                  90                  95

Glu Asp Pro Trp Thr Phe Gly Gly Gly Thr Lys Leu Glu Ile Lys
        100                 105                 110

<210> SEQ ID NO 23
<211> LENGTH: 124
<212> TYPE: PRT
<213> ORGANISM: Artificial Sequence
<220> FEATURE:
<223> OTHER INFORMATION: heavy chain variable region of 11B10

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
            20                  25                  30

Asn Met His Trp Val Lys Gln Ser His Gly Lys Ser Leu Glu Trp Ile
        35                  40                  45

Gly Lys Ile Tyr Pro Asn Asn Gly Val Thr Gly Tyr Asn Gln Glu Phe
    50                  55                  60

Arg Ser Lys Ala Thr Leu Thr Val Asp Asn Ser Ser Thr Ala Tyr
65                  70                  75                  80

Met Glu Leu Arg Ser Leu Thr Ser Glu Asp Ser Ala Ile Tyr Phe Cys
                85                  90                  95

Val Arg Ser Gly Ala Tyr Tyr Val Asn Tyr Leu Val Pro Tyr Phe Asp
            100                 105                 110

Tyr Trp Gly Gln Gly Thr Thr Leu Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: light chain variable region of 11B10

<400> SEQUENCE: 24

Asn Ile Val Leu Thr Gln Ser Pro Ala Ser Leu Ala Val Ser Pro Gly
1               5                   10                  15

Gln Arg Ala Thr Ile Ser Cys Arg Ala Ser Glu Ser Ile Asp Ile Tyr
            20                  25                  30

Gly Asn Ser Phe Met His Trp Tyr Gln Lys Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Asn Gly Ser Gly Ser Arg Thr Asp Phe Thr Leu Thr Ile Asp
65                  70                  75                  80

Pro Val Glu Gly Asp Asp Gly Ala Thr Tyr Tyr Cys Gln Gln Asn Tyr
                85                  90                  95

Glu Asp Pro Trp Thr Phe Gly Gly Gly Thr Lys Leu Glu Ile Lys
            100                 105                 110

<210> SEQ ID NO 25
<211> LENGTH: 357
<212> TYPE: DNA
<213> ORGANISM: Artificial Sequence
<220> FEATURE:
<223> OTHER INFORMATION: nucleotide sequence encoding VH of 12G6

<400> SEQUENCE: 25

```
gaggtccacc tgcaacagtc tggacctgag ctggtgaagc ctggggcttc agtgaagatg    60
tcctgtgagg cttctggata cacattcact gactactacg tggcctgggt gaagcagagc   120
cctggagaaa gctttgagtg gattggacgt gttaatcctt acagtggtgg tactagttac   180
aaccagaagt tcaagggcaa ggccacattg attgttgaca agtcctccag cacagcctac   240
atggagctca gcagcctgac atctgaggac tctgcggtct attactgtgc tagatgggac   300
tatggtgtct acgaggggta cattgactac tggggccaag ctccgctctc acagtc       357
```

<210> SEQ ID NO 26
<211> LENGTH: 321
<212> TYPE: DNA
<213> ORGANISM: Artificial Sequence
<220> FEATURE:
<223> OTHER INFORMATION: nucleotide sequence encoding VL of 12G6

<400> SEQUENCE: 26

```
gacatccaga tgactcagtc tccagcctcc ctatctgtat ctgtgggaga aactgtcacc    60
atcacatgtc gagcaagtga aaaatttac agtaatttag catggtatca gcagaaagag   120
ggaaaatctc ctcagctcct ggtctatgct gcaataagat tagcagatgg tgtgccatca   180
aggttcagtg gcagtggatc aggcacacag ttttccctca agatcaacag cctgcagtct   240
gaagattttg ggacttatta ctgtcaacat tttgggta ctcctctcac gttcggtgct   300
gggaccaagc tggagctgaa a                                             321
```

<210> SEQ ID NO 27
<211> LENGTH: 372
<212> TYPE: DNA
<213> ORGANISM: Artificial Sequence
<220> FEATURE:
<223> OTHER INFORMATION: nucleotide sequence encoding VH of 7G6

<400> SEQUENCE: 27

```
gaggtccagc ttcagcagtc aggacctgag ctggtgaaac ctggggcctc agtgaagata    60
tcctgcaagg cttctggata cacattcact gactacaaca tgcactgggt gaagcagagc   120
cttggaaaga gccttgagtg gattggatat atttatccta caatggtgg tactggctac   180 aatcagaagt tcgagagtaa ggccacattg actgtagaca attcctccag cacagcctac   240
atggagctcc gcaccctgac atctgaggac tctgcagtct attactgtgt aagatcagga   300
gcctactatt taactaccct agtccctac tttgactact ggggccaagg caccactctc   360
acagtctcct ca                                                       372
```

<210> SEQ ID NO 28
<211> LENGTH: 333
<212> TYPE: DNA
<213> ORGANISM: Artificial Sequence
<220> FEATURE:
<223> OTHER INFORMATION: nucleotide sequence encoding VL of 7G6

<400> SEQUENCE: 28

```
aacattgtgc tgacccaatc tccagcttct ttggctgtgt ctctagggca gagggccacc    60
atatcttgca gagccagtga aagtgttgat atttatggca atagtttat gcactggtac   120 cagcagaaac caggacagcc acccaaactc ctcatttatc ttgcatccaa actagaatgt   180
ggggtgtgtg ccaggttcaa tggcagtggg tgtaggacag acttcaccct cgctattgat   240
cctgtggagg gtgatgatgg tgcaacctat tactgtcagc aaaattatga ggatccgtgg   300
```
acgttcggtg gaggcaccaa gctggaaatc aaa                                      333

<210> SEQ ID NO 29
<211> LENGTH: 372
<212> TYPE: DNA
<213> ORGANISM: Artificial Sequence
<220> FEATURE:
<223> OTHER INFORMATION: nucleotide sequence encoding VH of 11B10

<400> SEQUENCE: 29
gaggtccagc ttcagcagtc aggacctgag ctggtgaaac ctggggcctc agtgaagata      60
tcctgcaagg cttctggata cacattcact ggctacaaca tgcactgggt gaagcagagc     120
catggaaaga gccttgagtg gattggaaaa atttatccta caatggtgt tactggctac      180 aaccaggagt tcaggagcaa ggccacattg actgtagaca attcctccag cacagcctac     240
atggagctcc gcagcctgac atctgaggac tctgcaatct atttctgtgt aagatcagga     300
gcctactatg ttaactacct agtccccctac tttgactact ggggccaagg caccactctc     360
acagtttcct ca                                                         372

<210> SEQ ID NO 30
<211> LENGTH: 333
<212> TYPE: DNA
<213> ORGANISM: Artificial Sequence
<220> FEATURE:
<223> OTHER INFORMATION: nucleotide sequence encoding VL of 11B10

<400> SEQUENCE: 30
aacattgtgc tgacccaatc tccagcctct ttggctgtgt ctccagggca gagggccacc      60
atatcctgca gagccagtga agtattgat atttatggca atagttttat gcactggtac      120
cagaagaaac caggacagcc acccaaactc ctcatttatc gtgcatccaa cctagaatct     180
ggggtccctg ccaggttcaa tggcagtggg tctaggacag acttcaccct caccattgat     240
cctgtggagg gtgatgatgg tgcaacctat tactgtcaac aaaattatga ggatccgtgg     300
acgttcggtg gaggtaccaa gctggaaatc aaa                                      333

<210> SEQ ID NO 31
<211> LENGTH: 25
<212> TYPE: DNA
<213> ORGANISM: Artificial Sequence
<220> FEATURE:
<223> OTHER INFORMATION: synthetic primer

<400> SEQUENCE: 31
ccgtttgkat ytccagcttg gtscc                                           25

<210> SEQ ID NO 32
<211> LENGTH: 25
<212> TYPE: DNA
<213> ORGANISM: Artificial Sequence
<220> FEATURE:
<223> OTHER INFORMATION: synthetic primer

<400> SEQUENCE: 32
cggtgaccgw ggtbccttgr cccca                                           25

<210> SEQ ID NO 33
<211> LENGTH: 29
<212> TYPE: DNA
<213> ORGANISM: Artificial Sequence
<220> FEATURE:

<223> OTHER INFORMATION: synthetic primer

<400> SEQUENCE: 33
atggactcca ggctcaattt agttttcct                                    29

<210> SEQ ID NO 34
<211> LENGTH: 29
<212> TYPE: DNA
<213> ORGANISM: Artificial Sequence
<220> FEATURE:
<223> OTHER INFORMATION: synthetic primer

<400> SEQUENCE: 34
atgaagttgc ctgttaggct gttggtgct                                    29

<210> SEQ ID NO 35
<211> LENGTH: 29
<212> TYPE: DNA
<213> ORGANISM: Artificial Sequence
<220> FEATURE:
<223> OTHER INFORMATION: synthetic primer

<400> SEQUENCE: 35
atggactcca ggctcaattt agttttcct                                    29

<210> SEQ ID NO 36
<211> LENGTH: 25
<212> TYPE: DNA
<213> ORGANISM: Artificial Sequence
<220> FEATURE:
<223> OTHER INFORMATION: synthetic primer

<400> SEQUENCE: 36
atggagacag acacactcct gctat                                        25

<210> SEQ ID NO 37
<211> LENGTH: 26
<212> TYPE: DNA
<213> ORGANISM: Artificial Sequence
<220> FEATURE:
<223> OTHER INFORMATION: synthetic primer

<400> SEQUENCE: 37
atgraatgsa sctgggtywt yctctt                                       26

<210> SEQ ID NO 38
<211> LENGTH: 27
<212> TYPE: DNA
<213> ORGANISM: Artificial Sequence
<220> FEATURE:
<223> OTHER INFORMATION: synthetic primer

<400> SEQUENCE: 38
atggtyctya tvtccttgct gttctgg                                      27

<210> SEQ ID NO 39
<211> LENGTH: 576
<212> TYPE: PRT
<213> ORGANISM: Influenza B Virus

<400> SEQUENCE: 39

Met Val Val Thr Ser Asn Ala Asp Arg Ile Cys Thr Gly Ile Thr Ser
1               5                   10                  15

Ser Asn Ser Pro His Val Val Lys Thr Ala Thr Gln Gly Glu Val Asn
            20                  25                  30

-continued

Val Thr Gly Val Ile Pro Leu Thr Thr Thr Pro Thr Lys Ser His Phe
         35                  40                  45

Ala Asn Leu Lys Gly Thr Glu Thr Arg Gly Lys Leu Cys Pro Lys Cys
     50                  55                  60

Leu Asn Cys Thr Asp Leu Asp Val Ala Leu Gly Arg Pro Lys Cys Thr
 65              70                  75                  80

Gly Asn Ile Pro Ser Ala Arg Val Ser Ile Leu His Glu Val Arg Pro
                 85                  90                  95

Val Thr Ser Gly Cys Phe Pro Ile Met His Asp Arg Thr Lys Ile Arg
             100                 105                 110

Gln Leu Pro Asn Leu Leu Arg Gly Tyr Glu His Ile Arg Leu Ser Thr
         115                 120                 125

His Asn Val Ile Asn Ala Glu Asn Ala Pro Gly Gly Pro Tyr Lys Ile
     130                 135                 140

Gly Thr Ser Gly Ser Cys Pro Asn Val Thr Asn Gly Asn Gly Phe Phe
145                 150                 155                 160

Ala Thr Met Ala Trp Ala Val Pro Lys Asn Asp Asn Asn Lys Thr Ala
                 165                 170                 175

Thr Asn Ser Leu Thr Ile Glu Val Pro Tyr Ile Cys Thr Glu Gly Glu
         180                 185                 190

Asp Gln Ile Thr Val Trp Gly Phe His Ser Asp Asn Glu Thr Gln Met
     195                 200                 205

Ala Lys Leu Tyr Gly Asp Ser Lys Pro Gln Lys Phe Thr Ser Ser Ala
 210                 215                 220

Asn Gly Val Thr Thr His Tyr Val Ser Gln Ile Gly Gly Phe Pro Asn
225                 230                 235                 240

Gln Thr Glu Asp Gly Gly Leu Pro Gln Ser Gly Arg Ile Val Val Asp
                 245                 250                 255

Tyr Met Val Gln Lys Ser Gly Lys Thr Gly Thr Ile Thr Tyr Gln Arg
         260                 265                 270

Gly Ile Leu Leu Pro Gln Lys Val Trp Cys Ala Ser Gly Lys Ser Lys
     275                 280                 285

Val Ile Lys Gly Ser Leu Pro Leu Ile Gly Glu Ala Asp Cys Leu His
 290                 295                 300

Glu Lys Tyr Gly Gly Leu Asn Lys Ser Lys Pro Tyr Tyr Thr Gly Glu
305                 310                 315                 320

His Ala Lys Ala Ile Gly Asn Cys Pro Ile Trp Val Lys Thr Pro Leu
                 325                 330                 335

Lys Leu Ala Asn Gly Thr Lys Tyr Arg Pro Pro Ala Lys Leu Leu Lys
         340                 345                 350

Glu Arg Gly Phe Phe Gly Ala Ile Ala Gly Phe Leu Glu Gly Gly Trp
     355                 360                 365

Glu Gly Met Ile Ala Gly Trp His Gly Tyr Thr Ser His Gly Ala His
 370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                 405                 410                 415

Leu Gln Arg Leu Ser Gly Ala Met Asp Glu Leu His Asn Glu Ile Leu
         420                 425                 430

Glu Leu Asp Glu Lys Val Asp Asp Leu Arg Ala Asp Thr Ile Ser Ser
     435                 440                 445

```
Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
                500                 505                 510

Ala Gly Glu Phe Ser Leu Pro Thr Phe Asp Ser Leu Asn Ile Thr Ala
                515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Phe His Ser
                565                 570                 575

<210> SEQ ID NO 40
<211> LENGTH: 579
<212> TYPE: PRT
<213> ORGANISM: Influenza B Virus

<400> SEQUENCE: 40

Met Val Val Thr Ser Asn Ala Asp Arg Ile Cys Thr Gly Ile Thr Ser
1               5                   10                  15

Ser Asn Ser Pro His Val Val Lys Thr Ala Thr Gln Gly Glu Val Asn
                20                  25                  30

Val Thr Gly Val Ile Pro Leu Thr Thr Thr Pro Thr Lys Ser His Phe
            35                  40                  45

Ala Asn Leu Lys Gly Thr Gln Thr Arg Gly Lys Leu Cys Pro Asn Cys
        50                  55                  60

Leu Asn Cys Thr Asp Leu Asp Val Ala Leu Gly Arg Pro Lys Cys Met
65                  70                  75                  80

Gly Thr Ile Pro Ser Ala Lys Ala Ser Ile Leu His Glu Val Lys Pro
                85                  90                  95

Val Thr Ser Gly Cys Phe Pro Ile Met His Asp Arg Thr Lys Ile Arg
                100                 105                 110

Gln Leu Pro Asn Leu Leu Arg Gly Tyr Glu Asn Ile Arg Leu Ser Ala
            115                 120                 125

Arg Asn Val Ile Asn Ala Glu Thr Ala Pro Gly Gly Pro Tyr Ile Val
    130                 135                 140

Gly Thr Ser Gly Ser Cys Pro Asn Val Thr Asn Gly Lys Gly Phe Phe
145                 150                 155                 160

Ala Thr Met Ala Trp Ala Val Pro Lys Asn Lys Asn Lys Thr Ala Thr
                165                 170                 175

Asn Pro Leu Thr Val Glu Val Pro Tyr Ile Cys Thr Lys Gly Glu Asp
            180                 185                 190

Gln Ile Thr Val Trp Gly Phe His Ser Asp Asn Glu Ala Gln Met Val
        195                 200                 205

Thr Leu Tyr Gly Asp Ser Lys Pro Gln Lys Phe Thr Ser Ser Ala Asn
    210                 215                 220

Gly Val Thr Thr His Tyr Val Ser Gln Ile Gly Gly Phe Pro Asn Gln
225                 230                 235                 240
```

```
Thr Glu Asp Glu Gly Leu Gln Gln Ser Gly Arg Ile Val Val Asp Tyr
                245                 250                 255

Met Val Gln Lys Pro Gly Lys Thr Gly Thr Ile Val Tyr Gln Arg Gly
                260                 265                 270

Val Leu Leu Pro Gln Lys Val Trp Cys Ala Ser Gly Arg Ser Lys Val
                275                 280                 285

Ile Lys Gly Ser Leu Pro Leu Ile Gly Glu Ala Asp Cys Leu His Glu
                290                 295                 300

Lys Tyr Gly Gly Leu Asn Lys Ser Lys Pro Tyr Tyr Thr Gly Glu His
305                 310                 315                 320

Ala Lys Ala Ile Gly Asn Cys Pro Ile Trp Val Lys Thr Pro Leu Lys
                325                 330                 335

Leu Ala Asn Gly Thr Lys Tyr Arg Pro Pro Ala Lys Leu Leu Lys Glu
                340                 345                 350

Arg Gly Phe Phe Gly Ala Ile Ala Gly Phe Leu Glu Gly Gly Trp Glu
                355                 360                 365

Gly Met Ile Ala Gly Trp His Gly Tyr Thr Ser His Gly Ala His Gly
        370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
                420                 425                 430

Leu Asp Glu Lys Val Asp Asp Leu Arg Ala Asp Thr Ile Ser Ser Gln
                435                 440                 445

Ile Glu Leu Ala Val Leu Leu Ser Asn Glu Gly Ile Ile Asn Ser Glu
                450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
                500                 505                 510

Gly Glu Phe Ser Leu Pro Thr Phe Asp Ser Leu Asn Ile Thr Ala Ala
                515                 520                 525

Ser Leu Asn Asp Asp Gly Leu Asp Asn His Thr Ile Leu Leu Tyr Tyr
                530                 535                 540

Ser Thr Ala Ala Ser Ser Leu Ala Val Thr Leu Met Ile Ala Ile Phe
545                 550                 555                 560

Ile Val Tyr Met Val Ser Arg Asp Asn Val Phe Leu Leu His Leu Ser
                565                 570                 575

Ile Arg Lys
```